United States Patent
Buschmann et al.

(10) Patent No.: US 8,669,399 B2
(45) Date of Patent: Mar. 11, 2014

(54) PROCESS FOR PREPARING SUBSTITUTED 3-(1-AMINO-2-METHYLPENTANE-3-YL) PHENYL COMPOUNDS

(75) Inventors: Helmut Heinrich Buschmann, Aachen (DE); Joerg Holenz, Enhoerna (SE)

(73) Assignee: Grünenthal GmbH, Aachen (DE)

( * ) Notice: Subject to any disclaimer, the term of this patent is extended or adjusted under 35 U.S.C. 154(b) by 8 days.

(21) Appl. No.: 13/160,050

(22) Filed: Jun. 14, 2011

(65) Prior Publication Data

US 2011/0306793 A1 Dec. 15, 2011

Related U.S. Application Data

(60) Provisional application No. 61/354,832, filed on Jun. 15, 2010.

(30) Foreign Application Priority Data

Jun. 15, 2010 (EP) .................................... 10006201

(51) Int. Cl.
- C07C 209/00 (2006.01)
- C07C 211/00 (2006.01)
- A01N 33/02 (2006.01)
- A61K 31/135 (2006.01)

(52) U.S. Cl.
USPC ........................... 564/375; 564/305; 514/649

(58) Field of Classification Search
None
See application file for complete search history.

(56) References Cited

U.S. PATENT DOCUMENTS

| 6,248,737 | B1 | 6/2001 | Buschmann et al. |
| 2002/0010178 | A1 | 1/2002 | Buschmann et al. |
| 2006/0167318 | A1 | 7/2006 | Jagusch et al. |
| 2006/0194988 | A1 | 8/2006 | Hell et al. |

FOREIGN PATENT DOCUMENTS

| CN | WO-2011080736 | * | 7/2011 | ............. A01N 33/02 |
| EP | 0 693 475 B1 | | 2/1998 | |
| WO | WO 2008/012046 A1 | | 1/2008 | |
| WO | WO 2008/012047 A1 | | 1/2008 | |

OTHER PUBLICATIONS

Goldschmidt et al., "Diphenyl Derivatives I. Basic 2-Diphenyl compounds related to the Morphine Molecule", Recueil Des Travaux Chimiques Des Pays-Bas, Elsevier Science Publishers, Amsterdam, NL, vol. 67, No. 6, Jan. 1, 1948, pp. 489-511 (twenty-three (23) sheets).

International Search Report (Form PCT/ISA/210 dated Jan. 25, 2012) including Form PCT/ISA/220 and PCT/ISA/237 (twenty (20) sheets).

Brunner et al., "Handbook of Enantioselective Catalysis with Transition Metal Compounds", vol. I: Products and Catalysts, 1993, Table of Contents (three (3) pages).

Jacobsen et al., "Comprehensive Asymmetric Catalysis I-III with Contributions by Numerous Experts", 1999, Table of Contents (eight (8) pages).

Noyori, "Catalytic Asymmetric Synthesis", Second Edition, 2000, Table of Contents (five (5) pages).

\* cited by examiner

*Primary Examiner* — Clinton Brooks

(74) *Attorney, Agent, or Firm* — Hunton & Williams LLP

(57) ABSTRACT

A process for the preparation of substituted 3-(1-amino-2-methylpentane-3-yl)phenyl compounds which has advantages over conventional processes with respect to higher conversions and yields, flexibility, a shorter overall route, environmentally acceptable conditions, influence of stereoselectivity such as diastereoselectivity in a targeted manner and at least partial suppression of the formation of undesired side-products and/or undesired stereoisomers, in particular undesired diastereomers.

14 Claims, No Drawings

PROCESS FOR PREPARING SUBSTITUTED 3-(1-AMINO-2-METHYLPENTANE-3-YL)PHENYL COMPOUNDS

CROSS REFERENCE TO RELATED APPLICATIONS

This application claims priority from co-pending U.S. provisional patent application No. 61/354,832 and from European patent application no. EP 10 006 201.7, both filed Jun. 15, 2010 and incorporated herein by reference.

BACKGROUND OF THE INVENTION

The present invention relates to a process for the preparation of substituted 3-(1-amino-2-methylpentane-3-yl)phenyl compounds.

A class of active ingredients having excellent analgesic effectiveness and very good tolerability are substituted 3-(1-amino-2-methylpentane-3-yl)phenyl compounds such as for example (3-(3-methoxyphenyl)-2-methyl-pentyl)dimethylamine which are inter alia known from EP 0 693 475 B1 and WO 2008/012047 A1.

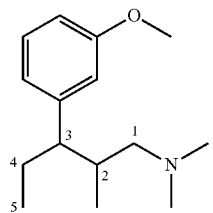 [SMILES: CCC(c1cccc(OC)c1)C(C)CN(C)C]

These compounds are conventionally prepared via a multi-step synthesis including a Mannich reaction as one of the key steps as it is exemplarily depicted below for the synthesis of (3-(3-methoxyphenyl)-2-methyl-pentyl)dimethylamine:

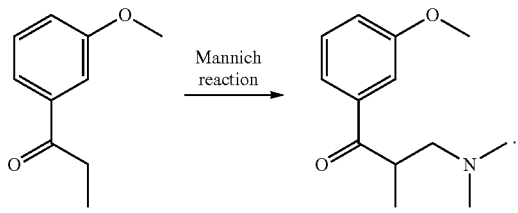 [SMILES: CCC(=O)c1cccc(OC)c1 ; COc1cccc(C(=O)C(C)CN(C)C)c1]

SUMMARY OF THE INVENTION

An object of the present invention was to provide an alternative process which allows for the preparation of substituted 3-(1-amino-2-methylpentane-3-yl)phenyl compounds. A further object of the present invention was to provide such a process that has advantages over conventional processes for the preparation of substituted 3-(1-amino-2-methylpentane-3-yl)phenyl compounds, in particular with respect to higher conversions and yields, flexibility, reducing the number of reaction steps, i.e. to a shorter overall route, environmentally acceptable conditions, influence of stereoselectivity such as diastereoselectivity in a targeted manner and at least partial suppression of the formation of undesired side-products and/or undesired stereoisomers, in particular undesired diastereomers.

These and other objects have been achieved by the invention described and claimed hereinafter, i.e. by:

a process for the preparation of a compound according to formula (I), optionally in the form of one of its isolated stereoisomers, in particular an enantiomer or diastereomer, a racemate or in form of a mixture of its stereoisomers, in particular enantiomers and/or diastereomers in any mixing ratio, or a physiologically acceptable acid addition salt thereof,

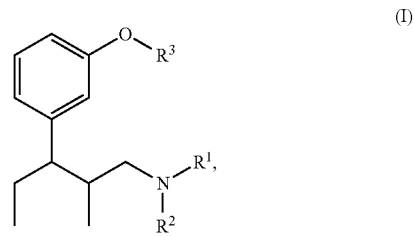

(I)

wherein $R^1$, $R^2$ and $R^3$ are each independently selected from the group consisting of H and $C_{1-4}$-aliphatic residues, according to alternative A comprising the steps of (a-I) hydrogenating a compound according to formula (A-II-a) or (A-I-b), wherein $R^1$, $R^2$ and $R^3$ in each case have the above defined meanings,

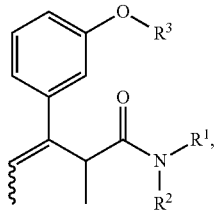

(A-I-a)

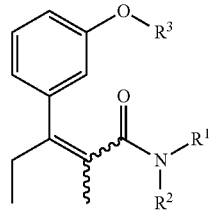

(A-I-b)

to a compound according to formula (A-II), wherein $R^1$, $R^2$ and $R^3$ have the above defined meanings,

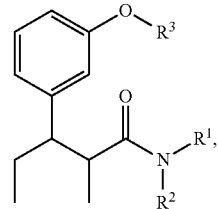

(A-II)

(a-II) reducing a compound according to formula (A-II) to a compound according to formula (I), (a-III) optionally converting the compound according to formula (I) into a physiologically acceptable acid addition salt thereof;

or according to alternative B comprising the steps of (b-I) converting a compound according to formula (B-I), wherein $R^3$ has the above defined meaning

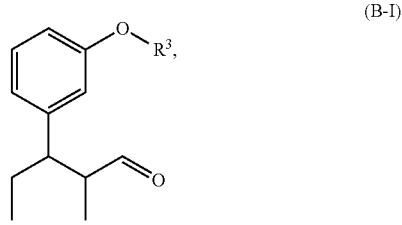

into a compound according to formula (I), wherein $R^1$, $R^2$ and $R^3$ have the above defined meanings, (b-II) optionally converting the compound according to formula (I) into a physiologically acceptable acid addition salt thereof, or according to alternative C comprising the steps of (c-I) hydrogenation of a compound according to formula (C-I), wherein $R^3$ has the above defined meaning

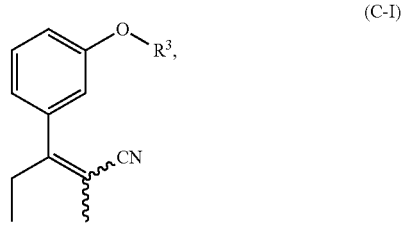

to a compound according to formula (C-II), wherein $R^3$ has the above defined meaning,

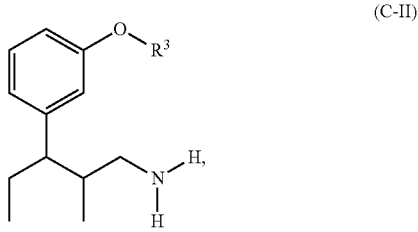

(c-II) optionally converting the thus obtained compound of formula (C-II) into a physiologically acceptable acid addition salt thereof or (c-III) optionally converting the thus obtained compound of formula (C-II) into a compound according to formula (I), and optionally converting the thus obtained compound according to formula (I) into a physiologically acceptable acid addition salt thereof.

It has been surprisingly found that by the process of the invention high conversions and yields can be achieved via a short reaction route and that the stereoselectivity, in particular diastereoselectivity can be influenced in a targeted manner by the choice of the reaction conditions and substrates. In particular, it has been surprisingly found that by the process of the invention the stereocenters may be established via substrate control with almost exclusive formation of the desired diastereomer(s), thus sparing elaborate purification or resolution steps to separate stereoisomers and costly chiral reagents, catalysts or ligands. The process of the invention does not require a Mannich reaction to be performed. In case of alternative A, a particular advantage is the presence of a carbonyl group in the intermediate products such as (A-I-a) and (A-II), which allows the performance of an isomerization and/or epimerization reaction by abstracting the acidic hydrogen atom at the carbon atom bound to the carbonyl group, and thus allows the synthesis of specific stereoisomers, in particular diastereomers in a targeted manner.

For the purpose of the specification, the term "$C_{1-4}$-aliphatic residue" refers to a saturated or unsaturated, linear or branched acyclic and unsubstituted hydrocarbon bearing 1 to 4, i.e. 1, 2, 3 or 4 carbon atoms and encompasses a $C_{1-4}$-alkyl group, a $C_{2-4}$-alkenyl group as well as a $C_{2-4}$-alkynyl group. A $C_{2-4}$-alkenyl has at least one C—C-double bond and a $C_{2-4}$-alkynyl has at least one C—C-triple bond. Examples of preferred $C_{1-4}$-aliphatic residues are methyl, ethyl, n-propyl, isopropyl, n-butyl, sec.-butyl, isobutyl, tert.-butyl, vinyl, allyl, butenyl, butadienyl, ethynyl and propargyl. A preferred "$C_{1-4}$-aliphatic residue" is a $C_{1-4}$-alkyl, more preferably a $C_{1-4}$-alkyl selected from the group consisting of methyl, ethyl, n-propyl, isopropyl, n-butyl, sec.-butyl, isobutyl, tert.-butyl, even more preferably selected from the group consisting of methyl and ethyl. A particularly preferred $C_{1-4}$-aliphatic residue is a methyl group.

For the purpose of the specification, the term "physiologically acceptable acid addition salt" refers to an acid addition salt of a compound such as a compound according to formula (I) and at least one inorganic or organic acid, which are—in particular when administered to a human and/or a mammal—physiologically acceptable. In principal, any suitable physiologically acceptable acid capable of forming such an addition salt may be used. Suitable physiologically acceptable acid addition salts include acid addition salts of inorganic acids, such as e.g. hydrogen chloride, hydrogen bromide and sulfuric acid, and salts of organic acids, such as methanesulfonic acid, fumaric acid, maleic acid, acetic acid, oxalic acid, succinic acid, malic acid, tartaric acid, mandelic acid, lactic acid, citric acid, glutaminic acid, acetylsalicylic acid, nicotinic acid, aminobenzoic acid, a-lipoic acid, hippuric acid and aspartic acid. The most preferred acid addition salt is a hydrochloride.

For the purpose of the specification, the symbol

"⌇"

used in formulas throughout the present application such as for example in formula (C-I) refers to a single bond between a first carbon atom forming a double bond with a second carbon atom and a substituent, indicating that the substituent bound to the first carbon atom may be either in trans- or in cis-position (or in (E)- or (Z)-position, respectively), with respect to the substituent(s) bound to the second carbon atom.

As used herein the term "isolated" when used with reference to a stereoisomer, diastereomer or enantiomer means substantially separated from the opposite stereoisomer, diastereomer or enantiomer, but not necessarily from other materials.

Preferably, in the compound according to formula (I) prepared by the process of the invention, $R^1$ and $R^2$ are each independently selected from the group consisting of H, methyl, ethyl, n-propyl, isopropyl, n-butyl, sec.-butyl, isobutyl, tert.-butyl, more preferably each independently selected from the group consisting of H and methyl, and $R^3$ is preferably selected from the group consisting of H, methyl, ethyl, n-propyl, isopropyl, n-butyl, sec.-butyl, isobutyl, tert.-butyl, more preferably selected from the group consisting of H and methyl, even more preferably denotes H.

In a preferred embodiment of the present invention, the compound according to formula (I) is a compound according to formula (Ib) as depicted below, optionally in the form of a physiologically acceptable acid addition salt, wherein $R^1$ and $R^2$ are each independently selected from the group consisting of H and $C_{1-4}$-aliphatic residues.

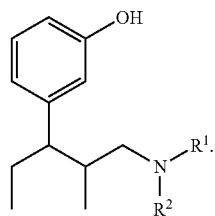
(Ib)

The present invention also relates to a process for the preparation of the stereoisomers of the compound of formula (I), such as enantiomers or diastereomers.

In another preferred embodiment of the present invention, the compound of formula (I) prepared by the process of the invention is a compound according to formulas (I-1), (I-2), (I-3) and/or (I-4) and any mixture in any mixing ratio thereof, optionally in the form of a physiologically acceptable acid addition salt, wherein $R^1$, $R^2$ and $R^3$ have one of the above defined meanings. Preferably, $R^3$ denotes H in each of formulas (I-1), (I-2), (I-3) and (I-4).

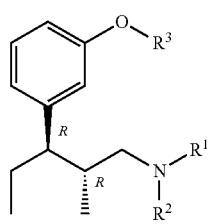
(I-1)

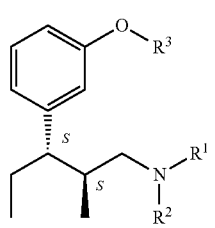
(I-2)

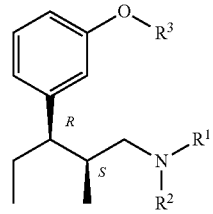
(I-3)

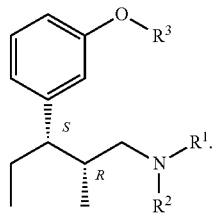
(I-4)

Preferred compounds prepared by the process of the invention are compounds according to formula (I-I) or (I-2) and any mixture in any mixing ratio thereof, optionally in the form of a physiologically acceptable acid addition salt, more preferably a compound of formula (I-I), optionally in the form of a physiologically acceptable acid addition salt.

In particular, the compound of formula (I) or (Ib) prepared by the process of the invention is a compound according to the formula (I-Ia), (I-2a), (I-3a) or (I-4a) or a mixture thereof in any mixing ratio, optionally in the form of a physiologically acceptable acid addition salt.

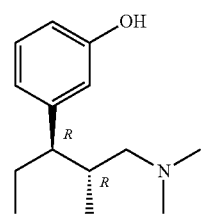
(I-1a)

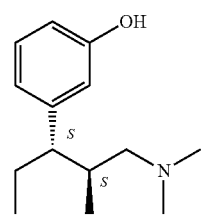
(I-2a)

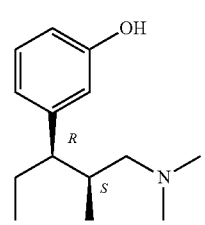
(I-3a)

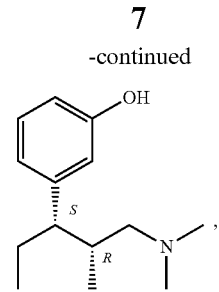

namely
(1R,2R)-3-(3-dimethylamino-1-ethyl-2-methyl-propyl)-phenol (I-1a),
(1S,2S)-3-(3-dimethylamino-1-ethyl-2-methyl-propyl)-phenol (I-2a),
(1R,2S)-3-(3-dimethylamino-1-ethyl-2-methyl-propyl)-phenol (I-3a),
(1S,2R)-3-(3-dimethylamino-1-ethyl-2-methyl-propyl)-phenol (I-4-a),
or any mixture thereof, optionally in the form of a physiologically acceptable acid addition salt.

Particularly preferred compounds prepared by the process of the invention are compounds according to formulas (I-1a) and/or (I-2a) and any mixture in any mixing ratio thereof, optionally in the form of a physiologically acceptable acid addition salt. The most preferred compound prepared by the process of the invention is a compound according to formula (I-1a), optionally in the form of a physiologically acceptable acid addition salt. The compound according to formula (I-1a) is also known as Tapentadol (CAS no. 175591-23-8).

Process According to Alternative A

The process of the invention according to alternative A comprises at least the steps (a-I) and (a-II), i.e. hydrogenation of a compound according to formula (A-I-a) or (A-I-b) to a compound according to formula (A-II) (step a-I), wherein $R^1$, $R^2$ and $R^3$ in each case have one of the above defined meanings, and reducing a compound according to formula (A-II) to a compound according to formula (I), wherein $R^1$, $R^2$ and $R^3$ in each case have one of the above defined meanings, (step a-II) as depicted in the following Scheme A1:

Scheme A1

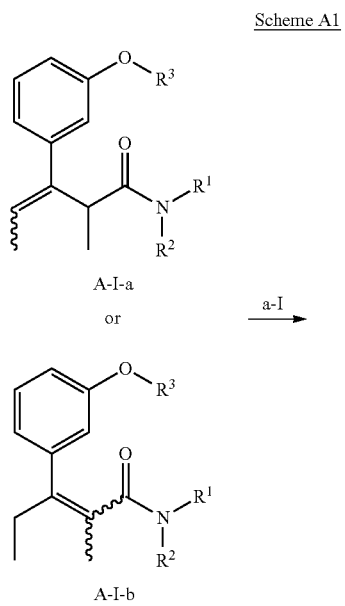

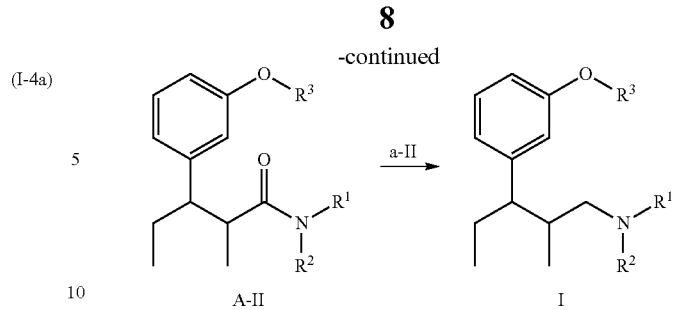

In a particularly preferred embodiment of the present invention, only a compound according to formula (A-I-b) is employed in step (a-I) of alternative A of the process of the invention.

In another particularly preferred embodiment of the present invention, only a compound according to formula (A-I-a) is employed in step (a-I) of alternative A of the process of the invention.

Step (a-I)

Preferably, the hydrogenation step (a-I) of the process of the invention according to alternative A is effected via heterogeneous or homogeneous catalysis, in each case in the presence of hydrogen. The hydrogen employed is preferably in gaseous form or at least part of it is dissolved in a liquid phase. In particular, the hydrogenation step (a-I) of the process of the invention according to alternative A is effected via heterogeneous catalysis.

The term catalyst within the context of the present invention includes both catalytically active materials themselves and inert materials that are provided with a catalytically active material. Accordingly, the catalytically active material can, for example, be applied to an inert carrier or can be present in a mixture with an inert material. There come into consideration as inert carrier or inert material, for example, carbon and other materials known to persons skilled in the art.

If a homogeneous catalyst in hydrogenation step (a-I) according to alternative A of the process of the invention is employed, said homogeneous catalyst is preferably a transition metal complex of rhodium, iridium or ruthenium, particularly preferably a transition metal complex of rhodium or iridium, more particularly a transition metal complex of rhodium with diphosphine ligands. Diphosphine ligands which may preferably be employed are known, for example, from the following literature references: a) H. Brunner, W. Zettlmeier, Handbook of Enantioselective Catalysis. VCH Weinheim, 1993, vol. 2; b) R. Noyori et al. in Catalytic Asymmetric Synthesis Second Edition (I. Ojima, Ed.), Wiley-VCH, Weinheim, 2000; c) E. N. Jacobsen, A. Pfaltz, H. Yamamoto (Eds.), Comprehensive Asymmetric Catalysis Vol I-III, Springer Berlin, 1999, and the references cited therein.

Particularly preferably the catalyst is selected from the group consisting of rhodium (−)-DIPAMP [(R,R)-(+1,2-Bis[(2-methoxyphenyl)(phenyl)phosphino]ethane], rhodium (+)-DIPAMP [(S,S)-(+)-1,2-Bis[(2-methoxyphenyl)(phenyl)phosphino]ethane], rhodium R-Solphos [R-(+)-N,N'-Dimethyl-7,7'-bis(diphenylphosphino)-3,3',4,4'-tetrahydro-8,8'-bi-2H-1,4-benzoxazine] and rhodium S-Solphos [S-(−)-N,N'-Dimethyl-7,7'-bis(diphenylphosphino)-3,3',4,4'-tetrahydro-8,8'-bi-2H-1,4-benzoxazine].

The reaction parameters for the homogeneous hydrogenation in step (a-I), such as, for example, pressure, temperature or reaction time, can vary over a wide range. Preferably, the temperature during the homogeneous hydrogenation in step (a-I) can be in each case from 0 to 250° C., particularly preferably from 5 to 100° C., very particularly preferably from 10 to 60° C. and most preferred from 15 to 25° C. The homogeneous hydrogenation in step (a-I) can preferably be carried out at reduced pressure, at normal pressure or at elevated pressure, preferably in the range from 0.01 to 300 bar. It is particularly preferred to carry out the reactions under pressure in a range of from 1 to 200 bar, in particular from 10 to 100 bar.

The reaction time can vary depending on various parameters, such as, for example, temperature, pressure, nature of the compound to be reacted or the properties of the catalyst, and can be determined for the process in question by persons skilled in the art using preliminary tests.

Heterogeneous catalysis within the context of the present invention means that the catalysts employed in heterogeneous catalysis are in each case present in the solid state of aggregation. If a heterogeneous catalyst in hydrogenation step (a-I) according to alternative A of the process of the invention is employed, said heterogeneous catalyst preferably comprises one or more transition metals, which can preferably be selected from the group consisting of Cu, Ag, Au, Zn, Cd, Hg, V, Nb, Ta, Cr, Mo, W, Fe, Ru, Os, Co, Rh, Ir, Ni, Pd and Pt, more preferably from the group consisting of Ru, Rh, Pd, Pt and Ni, and in particular from the group consisting of Pd, Pt and Ni. Preferably, heterogeneous catalysts according to the present invention can comprise one or more of the above-mentioned transition metals in the same or different oxidation states. It may also be preferable for the corresponding catalysts to contain one or more of the above-mentioned transition metals in two or more different oxidation states. The preparation of heterogeneous catalysts doped with transition metals can be carried out by conventional processes known to persons skilled in the art.

In particular, a heterogeneous catalyst is employed in hydrogenation reaction step (a-l) in alternative A of the process of the invention. Preferred heterogeneous catalysts employed in this steps are each independently selected from the group consisting of Raney nickel, palladium, palladium on carbon (1-10 wt. %, preferably 5 wt. %), platinum, platinum on carbon (1-10 wt. %, preferably 5 wt. %), ruthenium on carbon (1-10 wt. %, preferably 5 wt. %) and rhodium on carbon (1-10 wt. %, preferably 5 wt. %). Most preferred is palladium on carbon (1-10 wt. %, preferably 5 wt. %) as the catalyst for hydrogenation in step (a-I).

The compounds according to formula (A-I-a) or (A-I-b) according to the process of the invention are preferably in liquid phase and to that end are preferably mixed with or dissolved in a reaction medium that is liquid under the particular reaction conditions. Examples of suitable reaction media employed in hydrogenation reactions are methanol, ethanol, isopropanol, n-butanol, n-propanol, toluene, n-heptane, n-hexane, n-pentane, acetic acid, ethyl acetate, formic acid, hydrochloric acid, hydrobromic acid, sulfuric acid and any mixtures thereof. More preferably ethanol is used as the reaction medium in step (a-I). Of course, it is also possible to use mixtures or multiphase systems comprising two or more of the above-mentioned liquids in the processes according to the present invention. A reaction in supercritical $CO_2$ as reaction medium is also possible.

The reaction parameters for the hydrogenation reactions in step (a-I) such as, for example, pressure, temperature or reaction time, can independently of another vary over a wide range both. Preferably, the temperature during the heterogeneous hydrogenation in step (a-I) is in each case from 0 to 250° C., particularly preferably from 15 to 180° C. and very particularly preferably from 15 to 30° C. The heterogeneous hydrogenation in step (a-I) can preferably be carried out at reduced pressure, at normal pressure or at elevated pressure, preferably in the range from 0.5 to 300 bar. It is particularly preferred to carry out the reactions under pressure in a range from 0.5 to 10 bar, in particular from 0.75 to 10 bar. The reaction time can vary in dependence on various parameters, such as, for example, temperature, pressure, nature of the compound to be reacted or the properties of the catalyst, and can be determined for the process in question by persons skilled in the art using preliminary tests.

The continuous removal of samples in order to monitor the reaction, for example by means of gas chromatography (GC) methods, is also possible, optionally in combination with regulation of the corresponding process parameters.

The total amount of the heterogeneous catalyst(s) used depends on various factors, such as, for example, the ratio of the catalytically active component to any inert material present, or the nature of the surface of the catalyst(s). The optimal amount of catalyst(s) for a particular reaction can be determined by persons skilled in the art using preliminary tests.

The particular compound of formula (A-II) obtained in step (a-I) can be isolated and/or purified by conventional methods known to persons skilled in the art.

Step (a-II)

Preferably, the reduction step (a-II) of the process of the invention according to alternative A is performed in the presence of at least one suitable reducing agent. Any reducing agent suitable for the reduction of an amide group to an amine group may be employed. Preferably, the suitable reducing agent is at least one metal hydride, more preferably at least one metal hydride selected from the group consisting of lithium aluminium hydride (LAH), sodium borohydride, diisobutyl aluminium hydride (DIBAL), selectrides such as L-selectride, N-selectride and K-selectride, or the suitable reducing agent at least one borane such as borane-THF or the suitable reducing agent is hydrogen in combination with a catalyst, preferably in combination with a heterogeneous catalyst. Most preferred is lithium aluminium hydride.

Preferably, in step (a-II)—in addition to the reducing agent—at least one Lewis acid is employed in combination with the reducing agent. A particularly preferred Lewis acid is aluminium trichloride ($AlCl_3$).

Preferably, in step (a-II) the reducing agent, optionally in combination with a Lewis acid, is dissolved or suspended in a suitable reaction medium and then the compound according to formula (A-II), which is preferably dissolved in a suitable solvent, is added to the solution or suspension comprising the reducing agent and optionally the Lewis acid.

Suitable solvents for the compound according to formula (A-II) are preferably selected from the group consisting of methanol, ethanol, isopropanol, 1,4-dioxane, tetrahydrofuran (THF) and any mixtures in any ratio thereof. A particularly preferred solvent is THF.

Suitable reaction media for dissolving or suspending the reducing agent and optionally the Lewis acid are preferably selected from the group consisting of methanol, ethanol, n-propanol, isopropanol, 1,4-dioxane, tetrahydrofuran (THF) and any mixtures in any ratio thereof. A particularly preferred reaction medium is THF.

The reaction parameters for the reduction in step (a-II) such as, for example, pressure, temperature or reaction time, can independently of one another vary over a wide range both. Preferably, the temperature in step (a-II) is in each case from 0 to 250° C., particularly preferably from 15 to 180° C. and very particularly preferably from 15 to 80° C. The reduction in step (a-II) can preferably be carried out at reduced pressure, at normal pressure or at elevated pressure, preferably in the range from 0.5 to 300 bar, if hydrogen in combination with a catalyst is employed as reducing agent. It is particularly preferred to carry out the reactions under pressure in a range from 0.5 to 10 bar, in particular from 0.75 to 5 bar, bar, if hydrogen in combination with a catalyst is employed as reducing agent. The reaction time can vary in dependence on various parameters, such as, for example, temperature, pressure, nature of the compound to be reacted or the properties of the catalyst, and can be determined for the process in question by persons skilled in the art using preliminary tests.

The particular compound of formula (I) obtained in step (a-II) can be isolated and/or purified by conventional methods known to persons skilled in the art.

Preferably, when employing a compound according to formula (A-I-a) in step (a-I) of alternative A of the process of the invention, a compound according to formula (PI-3) and/or (PI-4) or any mixture in any mixing ratio thereof (as preferred embodiments of a compound according to formula (A-II)) as depicted below is obtained, wherein $R^1$, $R^2$ and $R^3$ have one of the above defined meanings. Consequently subjecting the compound according to formula (PI-3) and/or (PI-4) and any mixture in any mixing ratio thereof to reduction step (a-II) preferably yields a compound according to formulas (I-3) and/or (I-4) or any mixture in any mixing ratio thereof, wherein $R^1$, $R^2$ and $R^3$ have one of the above defined meanings.

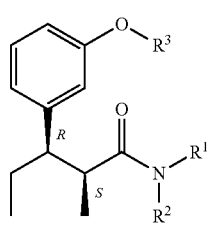
(PI-3)

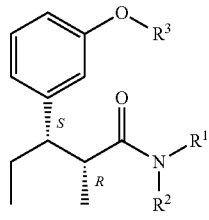
(PI-4)

Preferably, when employing a compound according to formula (A-I-b) in step (a-I) of alternative A of the process of the invention, a compound according to formula (PI-1) and/or (PI-2) or any mixture in any mixing ratio thereof (as preferred embodiments of a compound according to formula (A-II)) as depicted below is obtained, wherein $R^1$, $R^2$ and $R^3$ have one of the above defined meanings. Consequently subjecting the compound according to formula (PI-1) and/or (PI-2) or any mixture in any mixing ratio thereof, to reduction step (a-II) preferably yields a compound according to formula (I-1) and/or (I-2) or any mixture in any mixing ratio thereof, wherein $R^1$, $R^2$ and $R^3$ have one of the above defined meanings.

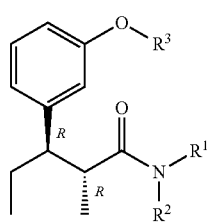
(PI-1)

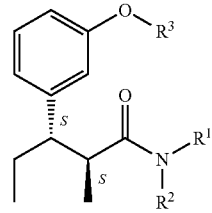
(PI-2)

In a particularly preferred embodiment of the present invention, only a compound according to formula (A-I-b) is employed in step (a-I) of alternative A of the process of the invention yielding a compound according to formulas (PI-1) and/or (PI-2) or any mixture in any mixing ratio thereof, wherein $R^1$, $R^2$ and $R^3$ have one of the above defined meanings. Preferably, only the compounds according to formula (PI-1) and/or (PI-2) or any mixture in any mixing ratio thereof, are employed in subsequent reduction step (a-II) yielding a compound according to formulas (I-1) and/or (I-2) or any mixture in any mixing ratio thereof, wherein $R^1$, $R^2$ and $R^3$ have one of the above defined meanings.

Step (a-III)

Optionally, the compound according to formula (I) may be converted into a physiologically acceptable acid addition salt thereof. The conversion of a compound according to formula (I) into a corresponding acid addition salt via reaction with a suitable acid or a suitable acid addition salt forming agent may be effected in a manner well known to those skilled in the art, e.g. by dissolving a compound according to formula (I) in at least one suitable solvent, preferably at least one solvent selected from the group consisting of acetone, benzene, n-butanol, 2-butanone, tert.-butyl methylether, chloroform, cyclohexane, diethyl ether, 1,4-dioxane, diisopropyl ether, alkyl acetates, e.g. ethyl acetate, ethanol, n-hexane, n-heptane, isopropanol, methanol, methylene chloride (dichloromethane), n-pentane, petrol ether, n-propanol, tetrahydrofuran, toluene, and any mixture in any mixing ratio thereof, and subsequent addition of at least one suitable acid or at least one acid addition salt forming agent. Preferably, the solvent employed for dissolving a compound according to formula (I) is a solvent in which the resulting acid addition salt of a compound according to formula (I) is not soluble.

The precipitation and/or crystallization of the acid addition salt may preferably be initiated and/or improved by cooling the corresponding reaction mixture and optionally partial evaporation of the solvent(s) under reduced pressure. The precipitate may then be filtered off, optionally washed with a suitable solvent, and if necessary further purified by recrystallization.

The salt formation may preferably be effected in a suitable solvent including diethyl ether, diisopropyl ether, dichloromethane, alkyl acetates, e.g. ethyl acetate, acetone, 2-butanone or any mixture thereof. Preferably a reaction with trimethylchlorosilane (trimethylsilylchloride) as acid addition salt forming agent in a suitable solvent may be used for the preparation of the corresponding hydrochloride addition salt.

Step (a-IV)

In a preferred embodiment of the process of the invention, alternative A further comprises a step (a-IV), wherein a compound according to formula (A-0), wherein $R^1$, $R^2$ and $R^3$ have one of the above defined meanings, is subjected to a dehydration reaction to obtain the compound according to formula (A-I-a),

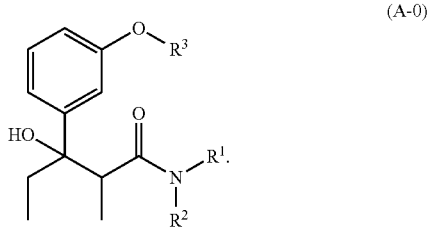

(A-0)

In Scheme A2 step (a-IV) is depicted below.

Scheme A2

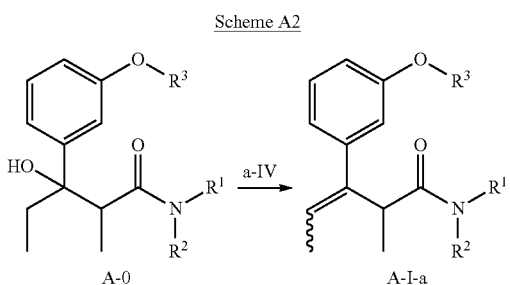

The dehydration step (a-IV) is preferably acid-catalyzed or acid-promoted, i.e. performed in the presence of an acid in a catalytically effective or at least stoichiometric amount. Preferably the acid is selected from the group consisting of formic acid, hydrochloric acid, acetic acid, sulfuric acid, hydrobromic acid, methanesulfonic acid or any mixture thereof. It is preferable if the acid is employed in a high concentration. Particularly preferably, hydrochloric acid and/or hydrobromic acid are employed. Preferably, the concentration of the hydrochloric acid or the hydrobromic acid is >20%, more preferably >30%, particularly preferably >35% by weight. Alternatively, the acid can also be used in gaseous form.

The compound of general formula (A-0) used in step (a-IV) according to the present invention is preferably in liquid phase and to that end is preferably mixed with or dissolved in a reaction medium that is liquid under the particular reaction conditions.

Examples of suitable reaction media include water, acetic acid, formic acid, toluene, hydrochloric acid, sulfuric acid, hydrobromic acid, methanesulfonic acid or any mixture thereof. Of course, it is also possible to use mixtures or multiphase systems comprising two or more of the above-mentioned liquids in the processes according to the present invention.

The reaction parameters for step (a-IV), such as, for example, pressure, temperature or reaction time, can vary over a wide range. It is preferable if the reaction temperature in step (a-IV) is between 15 and 100° C., particularly preferably between 18 and 80° C., more particularly preferably between 20 and 60° C. The dehydration step (a-IV) can preferably be carried out at reduced pressure, at normal pressure or at elevated pressure, preferably in the range from 0.01 to 300 bar. It is particularly preferred to carry out the reactions under pressure in a range from 0.5 to 5 bar, in particular from 0.5 to 1.5 bar.

The reaction time can vary depending on various parameters, such as, for example, temperature, pressure, nature of the compound to be reacted or the properties of the catalyst, and can be determined for the process in question by persons skilled in the art using preliminary tests. Preferably, the reaction time of step (a-IV) is between 2 and 25 h, particularly preferably between 3 and 22 h, more particularly preferably between 4 and 20 h.

The continuous removal of samples in order to monitor the reaction, for example by means of gas chromatographic (GC) methods, is also possible, optionally in combination with regulation of the corresponding process parameters.

The particular compound of general formula (A-I-a) obtained can be isolated and/or purified by conventional methods known to persons skilled in the art.

Alternatively, the dehydration step (a-IV) can also be carried out in the presence of at least one acidic catalyst, which can preferably be selected from the group consisting of ion-exchange resins, zeolites, heteropoly acids, phosphates, sulfates and optionally mixed metal oxides.

Preferably, the temperature for step (a-IV) when using an acidic catalyst as describe above is in each case from 20 to 250° C., particularly preferably from 50 to 180° C. and very particularly preferably from 100 to 160° C. The ratio of acidic catalyst and compound of formula (A-0) is preferably in the range from 1:200 to 1:1, in particular from 1:4 to 1:2. After the dehydration, the catalyst can be separated from the reaction mixture in a simple manner, preferably by filtration. The particular compound of general formula (A-I-a) obtained be isolated and/or purified by conventional methods known to persons skilled in the art.

Alternatively, the dehydration step (a-IV) can also be carried out by subjecting a compound of general formula (A-0) to an excess of thionyl chloride, optionally in a reaction medium, preferably in a reaction medium selected from the group consisting of diethylether, tetrahydrofuran, toluene, 2-methyltetrahydrofuran, dioxane, tert-butyl-methylether and any mixture thereof, and subsequent heating of the thus obtained reaction mixture to 40° C. to 120° C., preferably to 80° C. to 120° C.

Step (a-V)

In a preferred embodiment of the process of the invention, alternative A further comprises a step (a-V), wherein the compound according to formula (A-I-a) is subjected to an isomerization reaction, preferably in the presence of a base, to obtain a compound according to formula (A-I-b). In Scheme A3 step (a-V) is depicted below.

Scheme A3

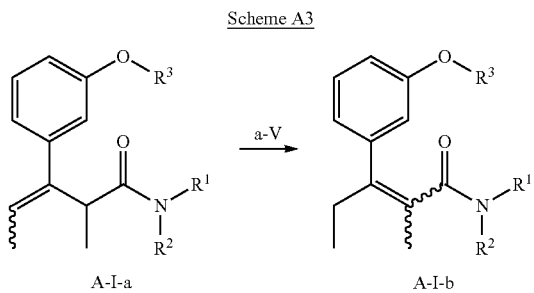

Suitable bases to be employed are any bases which are able to abstract the acidic proton of the carbon atom bound to the carbon atom of the carbonyl group of the compound according to formula (A-I-a).

Preferably, suitable bases which may be employed in step (a-V) are selected from the group consisting of 1,8-diazabi-cyclo[5.4.0]undec-7-ene (DBU), sodium hydride (NaH), potassium hydride, sodium hydroxide (NaOH), potassium hydroxide (KOH), amines, preferably tertiary amines, more preferably $N(C_{1-4}\text{-alkyl})_3$, even more preferably triethylamine, sodium methanolate, potassium tert-butylate (KOtBu) and mixtures of two of any of the aforementioned bases in any mixing ratio. The most preferred bases are selected from the group consisting of potassium tert-butylate, potassium hydroxide and sodium hydride. In particular, potassium tert-butylate is employed as a base.

Suitable reaction media for the conversion of a compound according to formula (A-I-a) into a compound to formula (A-I-b) are preferably selected from the group consisting of acetone, benzene, n-butanol, 2-butanone, tert.-butyl methylether, chloroform, cyclohexane, diethyl ether, 1,4-dioxane, diisopropyl ether, alkyl acetates, e.g. ethyl acetate, ethanol, n-hexane, n-heptane, isopropanol, methanol, methylene chloride (dichloromethane), n-pentane, petrol ether, n-propanol, tetrahydrofuran, toluene, and any mixture in any mixing ratio thereof. Preferably, THF is used as reaction medium.

The reaction parameters for step (a-V), such as, for example, pressure, temperature or reaction time, can vary over a wide range. It is preferable if the reaction temperature in step (a-V) is between 15 and 100° C., particularly preferably between 18 and 80° C. Preferably, step (a-V) is carried out at reduced pressure, at normal pressure or at elevated pressure, preferably in the range from 0.01 to 300 bar. It is particularly preferred to carry out the reactions under pressure in a range from 0.5 to 5 bar, in particular from 0.5 to 1.5 bar.

The reaction time can vary depending on various parameters, such as, for example, temperature, pressure, nature of the compound to be reacted and can be determined for the process in question by persons skilled in the art using preliminary tests. It is preferable if the reaction time of step (a-V) is between 2 and 25 h, particularly preferably between 3 and 22 h, more particularly preferably between 4 and 20 h.

The particular compound of general formula (A-I-b) obtained can be isolated and/or purified by conventional methods known to persons skilled in the art.

Step (a-VI)

In a particularly preferred embodiment of the process of the invention, alternative A further comprises a deprotection step (a-VI), wherein one of the compounds according to formula (A-0), (A-I-a), (A-I-b), (A-II) or (I), wherein $R^1$ and $R^2$ have in each case one of the above defined meanings and $R^3$ in each case is ≠H, is deprotected to obtain a compound according to formula (Ib). Preferably, the deprotection step (a-VI) is carried out by subjecting a compound according to formula (I) or (A-II), more preferably a compound according to formula (A-II), to said deprotection.

Preferably, at least one acid, preferably at least one acid selected from the group consisting of hydrobromic acid, hydrochloric acid and methanesulfonic acid is employed as deprotecting agent in step (a-VI). In case methanesulfonic acid is employed as acid a combination of methanesulfonic acid and methionine is preferably used as deprotecting agent. A combination of methanesulfonic acid and methionine is the most preferred deprotecting agent in step (a-VI). The deprotection step (a-VI) is preferably carried out in a reaction medium selected from the group consisting of diethylether, tetrahydrofuran, toluene, 2-methyltetrahydrofuran, dioxane, tert.-butyl methylether and any mixture thereof.

The reaction parameters for step (a-VI), such as, for example, pressure, temperature or reaction time, can vary over a wide range. It is preferable if the reaction temperature in step (a-VI) is between 15 and 100° C., particularly preferably between 18 and 80° C. Preferably, step (a-VI) is carried out at normal pressure.

The reaction time can vary depending on various parameters, such as, for example, temperature, pressure, nature of the compound to be reacted and can be determined for the process in question by persons skilled in the art using preliminary tests. It is preferable if the reaction time of step (a-VI) is between 2 and 25 h, particularly preferably between 3 and 22 h, more particularly preferably between 4 and 20 h.

The deprotected compound according to formula (Ib) can be isolated and/or purified by conventional methods known to persons skilled in the art.

Optionally, the compound according to formula (Ib) may be converted into a physiologically acceptable acid addition salt thereof according to the procedure previously described for step (a-III).

Step (a-VII)

In a preferred embodiment of the process of the invention, alternative A further comprises a step (a-VII-1) or (a-VII-2) for the preparation of a compound according to formula (A-0) as depicted in Scheme A4 below:

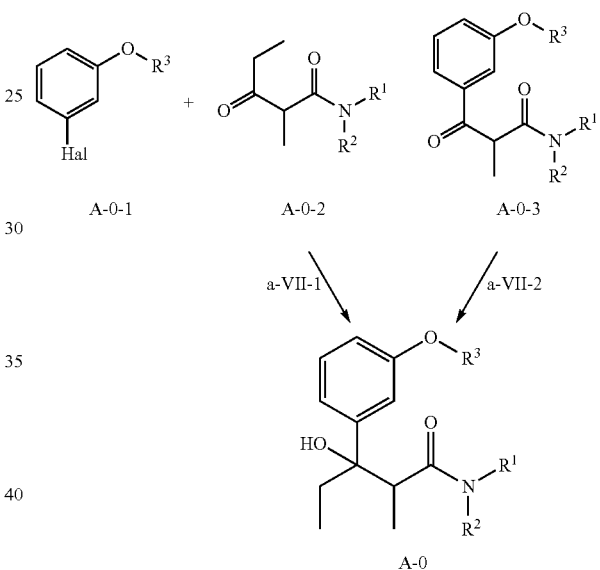

In step (a-VII-1) a magnesium halide, i.e. a Grignard reagent is formed from a compound according to formula (A-01), wherein Hal is a halogen atom, preferably selected from the group consisting of Cl, Br and I, in particular Br, and magnesium in an inert reaction medium. Said Grignard reagent is then reacted with a compound according to formula (A-02) under Grignard conditions in an inert reaction medium, preferably in an organic ether, for example, selected from the group consisting of diethyl ether, tetrahydrofuran, 2-methyltetrahydrofuran, tert-butylmethyl ether or any mixture thereof to obtain a compound according to formula (A0).

Alternatively, in step (a-VII-2) a compound according to formula (A03) is reacted with ethyl magnesium halide, preferably ethyl magnesium bromide or ethyl magnesium chloride, in an inert reaction medium, preferably in an organic ether, for example, selected from the group consisting of diethyl ether, tetrahydrofuran, 2-methyltetrahydrofuran, tert-butylmethyl ether or any mixture thereof under Grignard conditions, optionally in the presence of at least one Lewis acid, preferably at least one Lewis acid selected from the group consisting of $AlCl_3$ and cerium(III) chloride ($CeCl_3$), more preferably $CeCl_3$ to obtain a compound according to formula (A0). The reaction is particularly preferably carried out in tetrahydrofuran with ethyl magnesium chloride at a concentration from 0.5 M to 2 M of the ethyl magnesium chloride. Particularly preferably the reaction is carried out at a concentration of 1 M or 2 M of the ethyl magnesium chloride.

The particular compound of general formulas (A0) obtained can be isolated and/or purified by conventional methods known to persons skilled in the art.

Process According to Alternative B

The process of the invention according to alternative B comprises at least the step (b-I), i.e. a conversion of a compound according to formula (B-I), wherein $R^3$ has one of the above defined meanings, into a compound according to formula (I), wherein $R^1$, $R^2$ and $R^3$ in each case have one of the above defined meanings as depicted in Scheme B1 below:

Scheme B1

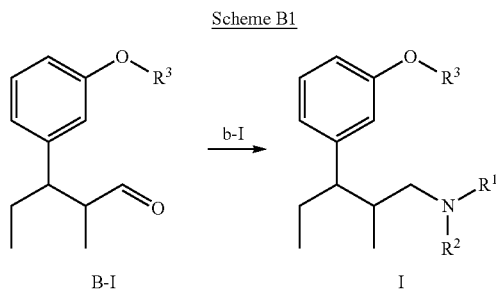

Step (b-I)

Preferably, step (b-I) is a reductive amination of a compound according to formula (B-I) to a compound according to formula (I) and is performed in the presence of H—$NR^1R^2$ and/or a salt thereof as amine component, wherein $R^1$ and $R^2$ have one of the above defined meanings, preferably both denote a methyl group, and at least one reducing agent. Any reducing agent suitable for the reduction amination of a compound bearing a carbonyl group such as an aldehyde group to a compound bearing an amine group may be employed. Preferably, the suitable reducing agent is at least one metal hydride, more preferably at least one metal hydride selected from the group consisting of sodium tetrahydridoborate ($NaBH_4$) and sodium trihydridocyanoborate ($NaBH_3(CN)$), in particular sodium trihydridocyanoborate. However, it is also possible to employ a metal such as iron, zinc or tin in combination with at least one acid, preferably at least one acid selected from the group consisting of acetic acid, hydrochloric acid and hydrobromic acid as reducing agent. Further, hydrogen in combination with a catalyst, preferably in combination with a heterogeneous catalyst may be employed as a suitable reducing agent. Moreover, a combination of formic acid and formaldehyde may be employed as a suitable reducing agent.

Most preferably, the suitable reducing agent is a combination of formic acid and formaldehyde. Such a combination of formic acid and formaldehyde has the advantage that—if $R^3$ in formula (B-I) denotes H, the resulting OH-group at the aromatic moiety of formula (B-I) will not be deprotonated. Further, by employing a combination of formic acid and formaldehyde as a suitable reducing agent, a compound of (I) will be obtained, wherein $R^1$ and $R^2$ both denote methyl.

Preferably, in step (b-I) the reducing agent, is dissolved or suspended in a suitable reaction medium together with the amine component and/or a salt thereof and then the compound according to formula (B-I), which is preferably dissolved in a suitable solvent, is added to the solution or suspension comprising the reducing agent and the amine component and/or a salt thereof.

Suitable solvents for the compound according to formula (B-I) are preferably selected from the group consisting of methanol, ethanol, isopropanol, 1,4-dioxane, tetrahydrofuran (THF) and any mixture in any ratio thereof. A particularly preferred solvent is methanol.

Suitable reaction media for dissolving or suspending the reducing agent and the amine component and/or a salt thereof are preferably selected from the group consisting of methanol, ethanol, n-propanol, isopropanol, 1,4-dioxane, tetrahydrofuran (THF) and any mixture in any ratio thereof. A particularly preferred reaction medium is methanol.

The reaction parameters for the reduction in step (b-I) such as, for example, pressure, temperature or reaction time, can independently of another vary over a wide range. Preferably, the temperature in step (b-I) is in each case from 0 to 250° C., particularly preferably from 15 to 180° C. and very particularly preferably from 15 to 80° C. The reduction in step (b-I) can preferably be carried out at reduced pressure, at normal pressure or at elevated pressure, preferably in the range from 0.5 to 300 bar. It is particularly preferred to carry out the reactions under pressure in a range from 0.5 to 10 bar, in particular from 0.75 to 5 bar. The reaction time can vary in dependence on various parameters, such as, for example, temperature, pressure, nature of the compound to be reacted or the properties of the catalyst, and can be determined for the process in question by persons skilled in the art using preliminary tests.

The particular compound of formula (I) obtained in step (b-I) can be isolated and/or purified by conventional methods known to persons skilled in the art.

Step (b-II)

Optionally, the compound according to formula (I) may be converted into a physiologically acceptable acid addition salt thereof in step (b-II). The conversion of a compound according to formula (I) into a corresponding acid addition salt may be carried out has it has been previously described in step (a-III) according to alternative A of the process of the invention.

Step (b-III)

In a particularly preferred embodiment of the process of the invention, alternative B further comprises a deprotection step (b-III), wherein the compound according to formula (I), wherein $R^1$ and $R^2$ have in each case have one of the above defined meanings and $R^3$ in each case is ≠H, is deprotected to obtain a compound according to formula (Ib). Preferably, the deprotection step (b-III) is carried out as it has been previously described in step (a-VI) according to alternative A of the process of the invention.

Step (b-IV)

In a preferred embodiment of the process of the invention, alternative B further comprises a step (b-IV) for the preparation of a compound according to formula (B-I) as depicted in the following Scheme B2:

Scheme B2

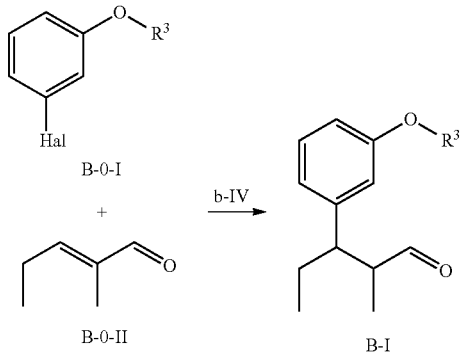

Preferably, step (b-IV) is an 1,4-addition reaction of an α,β-unsaturated carbonyl compound (B-0-II) and a compound according to formula (B-0-I).

In a preferred embodiment of step (b-IV) a metal halide, preferably a magnesium halide, is first formed from a compound according to formula (B-0-I), wherein Hal is a halogen atom, preferably selected from the group consisting of Cl, Br and I, in particular Br, and a metal, preferably magnesium to form a Grignard reagent, in an inert reaction medium. Suitable reaction media for producing said metal halide are preferably selected from the group consisting of diethyl ether, diisopropyl ether, 1,4-dioxane, tetrahydrofuran (THF) and any mixtures in any ratio thereof. A particularly preferred reaction medium is THF. The thus obtained metal halide is then converted into an organocopper compound by reaction with a suitable copper precursor compound, preferably a copper(I)-compound, more preferably selected from the group consisting of copper(I) halides, in particular copper(I) iodide, copper(I) bromide or copper(I) chloride, and copper(I) cyanide. The thus obtained organocopper compound is then reacted with a compound (B-0-II), preferably dissolved or suspended in a suitable reaction medium, preferably selected from the group consisting of diethyl ether, diisopropyl ether, 1,4-dioxane, tetrahydrofuran (THF) and any mixture in any ratio thereof to obtain a compound according to formula (B-I).

In another preferred embodiment of step (b-IV), an organometal compound, preferably an organolithium compound, is first formed from a compound according to formula (B-01), wherein Hal is a halogen atom, preferably selected from the group consisting of Cl, Br and I, in particular Br, and a suitable organometallic precursor compound, preferably an $C_{1-4}$-alkyl lithium compound, more preferably n-butyl lithium in an inert reaction medium. Suitable reaction media for producing said organometal compound are preferably selected from the group consisting of diethyl ether, diisopropyl ether, 1,4-dioxane, tetrahydrofuran (THF) and any mixtures in any ratio thereof. A particularly preferred reaction medium is THF. The thus obtained organometal compound is then converted into an organocopper compound by reaction with a suitable copper precursor compound, preferably a copper(I)-compound, more preferably selected from the group consisting of copper(I) halides, in particular copper(I) iodide, copper(I) bromide or copper(I) chloride, and copper(I) cyanide. The thus obtained organocopper compound is then reacted with a compound (B-0-II), preferably dissolved or suspended in a suitable reaction medium, preferably selected from the group consisting of diethyl ether, diisopropyl ether, 1,4-dioxane, tetrahydrofuran (THF) and any mixture in any ratio thereof to obtain a compound according to formula (B-I).

The particular compound of formula (B-I) obtained in step (b-IV) can be isolated and/or purified by conventional methods known to persons skilled in the art.

Process According to Alternative C

The process of the invention according to alternative C comprises at least the step (c-I), i.e. hydrogenation of a compound according to formula (C-I) to a compound according to formula (C-II) (step c-I), wherein $R^3$ in each case has one of the above defined meanings, and optionally converting the thus obtained compound of formula (C-II) into a physiologically acceptable acid addition salt thereof (step c-II) or optionally converting the resulting compound of formula (C-II) into a compound according to formula (I), and optionally converting the thus obtained compound according to formula (I) into a physiologically acceptable acid addition salt thereof. Steps (c-I) and (c-III) are depicted in the following Scheme C1:

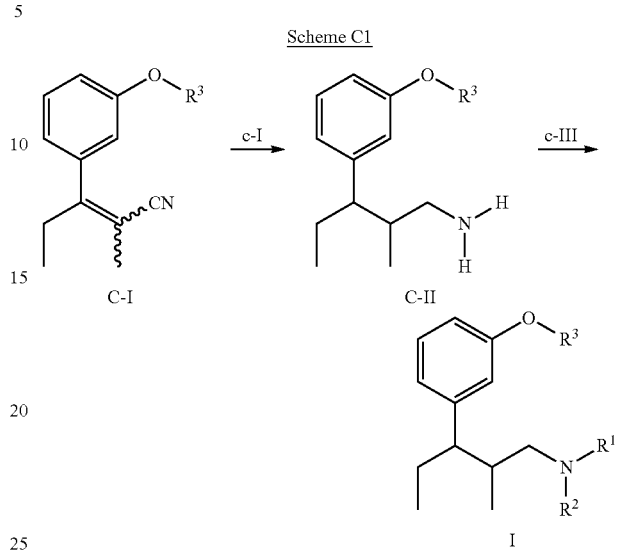

Step (c-I)

Preferably, the hydrogenation step (c-I) of the process of the invention according to alternative C is effected via heterogeneous or homogeneous catalysis, in each case in the presence of hydrogen. The hydrogen employed is preferably in gaseous form or at least part of it is dissolved in a liquid phase. In particular, the hydrogenation step (c-I) of the process of the invention according to alternative A is effected via heterogeneous catalysis.

If a homogeneous catalyst in hydrogenation step (c-I) according to alternative C of the process of the invention is employed, the same homogeneous catalysts as well as the same reaction parameters may be applied which may be also used for the hydrogenation reaction of step (a-I) of alternative A of the process of the invention.

If a heterogeneous catalyst in hydrogenation step (c-I) according to alternative C of the process of the invention is employed, the same heterogeneous catalysts as well as the same reaction parameters may be applied which may be also used for the hydrogenation reaction of step (a-I) of alternative A of the process of the invention.

In particular, a heterogeneous catalyst is employed in hydrogenation reaction step (c-I) in alternative C of the process of the invention. Preferred heterogeneous catalysts employed in this step are each independently selected from the group consisting of Raney nickel, palladium, palladium on carbon (1-10 wt. %, preferably 5 wt. %), platinum, platinum on carbon (1-10 wt. %, preferably 5 wt. %), ruthenium on carbon (1-10 wt. %, preferably 5 wt. %) and rhodium on carbon (1-10 wt. %, preferably 5 wt. %). Most preferred is Raney Nickel as the catalyst for hydrogenation in step (c-I).

The compound according to formula (C-I) according to the process of the invention is preferably in liquid phase and to that end are preferably mixed with or dissolved in a reaction medium that is liquid under the particular reaction conditions. Examples of suitable reaction media employed in hydrogenation reactions are methanol, ethanol, isopropanol, n-butanol, propanol, toluene, n-heptane, n-hexane, n-pentane, acetic acid, ethyl acetate, formic acid, hydrochloric acid, hydrobromic acid, sulfuric acid and mixtures thereof. More preferably methanol is used as the reaction medium in step (c-I). Of course, it is also possible to use mixtures or multiphase systems comprising two or more of the above-mentioned liquids in the processes according to the present invention.

The reaction parameters for the hydrogenation reaction via heterogeneous catalysis in step (c-I) such as, for example, pressure, temperature or reaction time, can independently of another vary over a wide range both. Preferably, the temperature during the heterogeneous hydrogenation in step (c-I) is in each case from 0 to 250° C., particularly preferably from 15 to 180° C. and very particularly preferably from 15 to 30° C. The heterogeneous hydrogenation in step (c-I) can preferably be carried out at reduced pressure, at normal pressure or at elevated pressure, preferably in the range from 0.5 to 300 bar. It is particularly preferred to carry out the reactions under pressure in a range from 0.5 to 10 bar, in particular from 0.75 to 10 bar. The reaction time can vary in dependence on various parameters, such as, for example, temperature, pressure, nature of the compound to be reacted or the properties of the catalyst, and can be determined for the process in question by persons skilled in the art using preliminary tests.

The continuous removal of samples in order to monitor the reaction, for example by gas chromatography (GC) methods, is also possible, optionally in combination with regulation of the corresponding process parameters.

The total amount of the heterogeneous catalyst(s) used depends on various factors, such as, for example, the ratio of the catalytically active component to any inert material present, or the nature of the surface of the catalyst(s). The optimal amount of catalyst(s) for a particular reaction can be determined by persons skilled in the art using preliminary tests.

The particular compound of formula (C-II) obtained in step (c-I) can be isolated and/or purified by conventional methods known to persons skilled in the art.

Step (c-II)

The compound according to formula (C-II) obtained in step (c-I) corresponds to a compound according to formula (I), wherein $R^1$ and $R^2$ both denote H.

Optionally, the compound according to formula (C-II) may be converted into a physiologically acceptable acid addition salt thereof in step (c-II).

The conversion of a compound according to formula (C-II) into a corresponding acid addition salt may be carried out has it has been previously described for the conversion of a compound according to formula (I) into a physiologically acceptable acid addition salt thereof in step (a-III) according to alternative A of the process of the invention.

Step (c-III)

Optionally, the compound according to formula (C-II) may be converted into a compound according to formula (I) in step (c-III), i.e. in a compound according to formula (I), wherein at least one of $R^1$ and $R^2$ denotes a $C_{1-4}$-aliphatic residue.

Any method suitable for substituting at least one hydrogen atom of a primary amine group with a $C_{1-4}$-aliphatic residue may be performed in step (c-III).

In a preferred embodiment, a compound according to formula (C-II) may be subjected to a reaction with a compound halogen substituted $C_{1-4}$-aliphatic compound, preferably a halogen substituted $C_{1-4}$-alkyl compound ($C_{1-4}$.alkyl-Hal), wherein Hal in each case is preferably selected from the group consisting of Cl, Br and I to obtain a compound according to formula (I), wherein at least one of $R^1$ and $R^2$ denotes a $C_{1-4}$-aliphatic residue.

In another preferred embodiment, a compound according to formula (C-II) may be subjected to an Eschweiler-Clarke reaction in step (c-III). Preferably, a compound according to formula (C-II) is reacted with formaldehyde or a formaldehyde source such as paraformaldehyde, thereby generating a corresponding imine compound which is then further reacted with an acid, preferably an organic acid, more preferably, formic acid, thereby generating a compound according to formula (I), wherein at least one of $R^1$ and $R^2$ denotes a $C_{1-4}$-aliphatic residue, preferably both $R^1$ and $R^2$ denote a $C_{1-4}$-aliphatic residue, even more preferably both $R^1$ and $R^2$ denote a methyl group. Alternatively, a compound according to formula (C-II) is reacted with formaldehyde or a formaldehyde source such as paraformaldehyde, thereby generating a corresponding imine compound which is then further reacted with an hydrogen in combination with a catalyst, thereby generating a compound according to formula (I), wherein at least one of $R^1$ and $R^2$ denotes a $C_{1-4}$-aliphatic residue, preferably both $R^1$ and $R^2$ denote a $C_{1-4}$-aliphatic residue, even more preferably both $R^1$ and $R^2$ denote a methyl group.

Optionally, the thus obtained compound according to formula (I) may then be converted into a physiologically acceptable acid addition salt thereof, as has it has been previously described in step (a-III) according to alternative A of the process of the invention.

Steps (c-IV) and (c-V)

In a preferred embodiment of the process of the invention, alternative C further comprises a step (c-IV), wherein a compound of formula (C-0-I) is subjected to a desilylation reaction, wherein $R^3$ is selected from the group consisting of H and a $C_{1-4}$-aliphatic residue, and wherein $R^a$, $R^b$ and $R^c$ are independently selected from the group consisting of $C_{1-8}$-aliphatic residues and aryl, preferably independently of another denote a $C_{1-8}$-aliphatic residue, even more preferably each denote methyl,

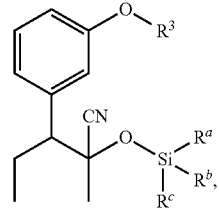

(C-0-I)

yielding a compound according to formula (C-0-II), wherein $R^3$ has the above defined meaning,

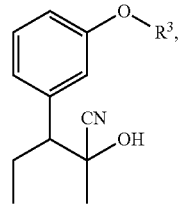

(C-0-II)

and a step (c-V), wherein a compound of formula (C-0-II) is subjected to a dehydration reaction yielding the compound according to formula (C-I). Steps (c-IV) and (c-V) are depicted in the following Scheme C2:

Scheme C2

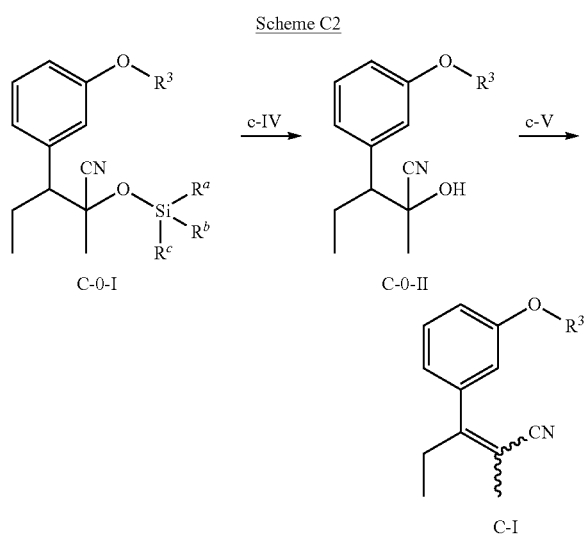

In a preferred embodiment of the present invention, the compound according to formula (C-0-II) is not isolated, i.e. a compound according to formula (C-O-I) can be directly transformed into a compound according to formula (C-I) in one step, i.e. steps (c-IV) and (c-V) can be carried out in one step (c-IV-V).

The desilylation step (c-IV) is preferably acid-catalyzed or acid-promoted or performed in the presence of a fluoride source such as potassium fluoride or cesium fluoride or tributylammonium fluoride. Alternatively, in case $R^a$, $R^b$ and $R^c$ each denote methyl, (c-IV) may also be performed in the presence of a base, preferably an inorganic base such as potassium carbonate. However, in a most preferred embodiment desilylation step (c-IV) is performed in the presence of an acid in a catalytically effective or at least stoichiometric amount. Preferably the acid is selected from the group consisting of formic acid, hydrochloric acid, acetic acid, sulfuric acid, hydrobromic acid, methanesulfonic acid, phosphoric acid or any mixture thereof. It is preferable if the acid is employed in a high concentration. Particularly preferably, hydrochloric acid is employed.

Examples of suitable reaction media for (c-IV) include lower alcohols such as methanol or ethanol as well as THF, 1,4-dioxane or any mixture thereof. Of course, it is also possible to use mixtures or multiphase systems comprising two or more of the above-mentioned liquids in the processes according to the present invention.

The particular compound of general formula (C-0-II) obtained can be isolated and/or purified by conventional methods known to persons skilled in the art The dehydration step (c-V) is preferably acid-catalyzed or acid-promoted, i.e. performed in the presence of an acid in a catalytically effective or at least stoichiometric amount. Preferably the acid is selected from the group consisting of formic acid, hydrochloric acid, acetic acid, sulfuric acid, hydrobromic acid, methanesulfonic acid, p-toluenesulfonic acid, phosphorous pentoxide, thionyl chloride, phosphoryl chloride or any mixture thereof. It is preferable if the acid is employed in a high concentration. Particularly preferably, phosphoryl chloride is employed.

The compound of general formula (C-0-II) used in step (c-V) according to the present invention is preferably in liquid phase and to that end is preferably mixed with or dissolved in a reaction medium that is liquid under the particular reaction conditions.

Examples of suitable reaction media include acetic acid, formic acid, toluene, pyridine, hydrochloric acid, sulfuric acid, hydrobromic acid, methanesulfonic acid, p-toluenesulfonic acid, phosphorous pentoxide, thionyl chloride, phosphoryl chloride or any mixture thereof. Of course, it is also possible to use mixtures or multiphase systems comprising two or more of the above-mentioned liquids in the processes according to the present invention. Preferably, step (c-V) is performed in pyridine as a reaction medium in the presence of phosphoryl chloride.

The reaction parameters for step (c-V), such as, for example, pressure, temperature or reaction time, can vary over a wide range. It is preferable if the reaction temperature in step (c-V) is between 15 and 100° C., particularly preferably between 18 and 90° C. The dehydration step (c-V) can preferably be carried out at reduced pressure, at normal pressure or at elevated pressure, preferably in the range from 0.01 to 300 bar. It is particularly preferred to carry out the reaction under pressure in a range from 0.5 to 5 bar, in particular from 0.5 to 1.5 bar.

The reaction time can vary depending on various parameters, such as, for example, temperature, pressure, nature of the compound to be reacted or the properties of the catalyst, and can be determined for the process in question by persons skilled in the art using preliminary tests. Preferably, the reaction time of step (c-V) is between 2 and 25 h, particularly preferably between 3 and 22 h, more particularly preferably between 4 and 20 h.

The continuous removal of samples in order to monitor the reaction, for example by means of gas chromatographic (GC) methods, is also possible, optionally in combination with regulation of the corresponding process parameters.

The particular compound of general formula (C-I) obtained can be isolated and/or purified by conventional methods known to persons skilled in the art.

Step (c-VI)

In a particularly preferred embodiment of the process of the invention, alternative C further comprises a deprotection step (c-VI), wherein one of the compounds according to formula (C-I), (C-II), (C-O-I), (C-O-II) or (I), wherein $R^1$ and $R^2$ have in each case have one of the above defined meanings and $R^3$ in each case is ≠H, is deprotected to obtain a compound according to formula (Ib). Preferably, the deprotection step (c-VI) is carried out by subjecting a compound according to formula (I), (C-I), or (C-II), more preferably a compound according to formula (C-I), to said deprotection.

Preferably, at least one acid, preferably at least one acid selected from the group consisting of hydrobromic acid, hydrochloric acid and methanesulfonic acid is employed as deprotecting agent in step (c-VI). In case methanesulfonic acid is employed as acid a combination of methanesulfonic acid and methionine is preferably used as as deprotecting agent. A combination of methanesulfonic acid and methionine is the most preferred deprotecting agent in step (c-VI). The deprotection step (c-VI) is preferably carried out in a reaction medium selected from the group consisting of diethylether, tetrahydrofuran, toluene, 2-methyltetrahydrofuran, dioxane, tert.-butyl methylether and any mixture thereof.

The reaction parameters for step (c-VI), such as, for example, pressure, temperature or reaction time, can vary over a wide range. It is preferable if the reaction temperature in step (c-VI) is between 15 and 100° C., particularly preferably between 18 and 80° C. Preferably, step (c-VI) is carried out at normal pressure.

The reaction time can vary depending on various parameters, such as, for example, temperature, pressure, nature of the compound to be reacted and can be determined for the process in question by persons skilled in the art using preliminary tests. It is preferable if the reaction time of step (c-VI) is between 2 and 25 h, particularly preferably between 3 and 22 h, more particularly preferably between 4 and 20 h.

The particular deprotected compound of formula (Ib) can be isolated and/or purified by conventional methods known to persons skilled in the art.

Step (c-VII)

In a preferred embodiment of the process of the invention, alternative C further comprises a step (c-VII) for the preparation of a compound according to formula (C-O-I) as depicted in the following Scheme C4:

Scheme C4

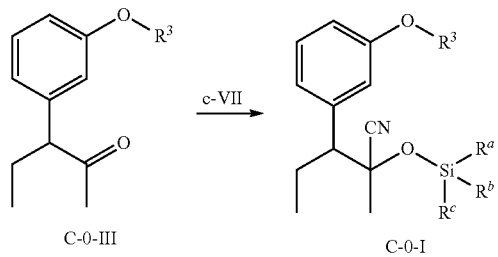

In step (c-VII) a compound according to formula (C-0-111), wherein $R^3$ has one of the above defined meanings, is reacted with a compound having the formula $SiR^aR^bR^b(CN)$, wherein $R^a$, $R^b$ and $R^c$ are each independently selected from the group consisting of $C_{1-8}$-aliphatic residues and aryl, preferably independently of another denote a $C_{1-8}$-aliphatic residue. Preferably the compound $SiR^aR^bR^c(CN)$ is selected from the group consisting of trimethylsilylcyanide, triethylsilylcyanide, tri-n-propylsilylcyanide and triisopropylsilylcyanide. Most preferred is trimethylsilylcyanide.

A suitable reaction medium for step (c-VII) is preferably at least one reaction medium selected from the group consisting of acetone, benzene, n-butanol, 2-butanone, tert.-butyl methylether, chloroform, cyclohexane, diethyl ether, 1,4-dioxane, diisopropyl ether, alkyl acetates, e.g. ethyl acetate, ethanol, n-hexane, n-heptane, isopropanol, methanol, methylene chloride (dichloromethane), n-pentane, petrol ether, n-propanol, tetrahydrofuran, toluene and any mixture in any mixing ratio thereof. Most preferred reaction media are n-hexane and n-heptane.

Preferably, step (c-VII) of the process of the invention according to alternative C is performed in the presence of at least metal halide, preferably at least one transition metal halide, wherein the halide is preferably selected from the group consisting of chloride, bromide and iodide. Most preferred is a zinc halide, in particular zinc iodide ($ZnI_2$).

The thus obtained compound according to formula (C-0-I) of can be isolated and/or purified by conventional methods known to persons skilled in the art.

Any stereoisomers of any compounds obtained via alternatives A, B or C of the process of the invention, such as e.g. a compound according to any of the formulas (I-1), (I-2), (I-3), (I-4), (I-1a), (I-2a), (I-3a), (I-4-a), (PI-1), (PI-2), (PI-3) and (PI-4) may be separated from each other at any time of each reaction sequence and/or purified by conventional methods known to a person skilled in the art. Preferably, LC (liquid chromatography) techniques, more preferably HPLC (high performance liquid chromatography) techniques, even more preferably semi-preparative or preparative HPLC techniques may be used for the separation of these stereoisomers. Alternatively, fractionized crystallization of any mixture of these stereoisomers may be carried out to separate any unwanted stereoisomers.

The steps according to each of the three alternatives according to the present invention can be carried out discontinuously (batchwise) or continuously, preference being given to the discontinuous procedure.

There come into consideration as the reactor for the discontinuous procedure, for example, a slurry reactor, and for the continuous procedure a fixed-bed reactor or loop reactor.

EXAMPLES

In the following, the present invention is illustrated by a number of examples for each of the alternatives A to C of the process of the invention. The examples are only illustrative do not limit the scope of the invention.

| Abbreviations used in the Examples | |
|---|---|
| AIBN: | azo-bis-isobutyronitrile |
| AlCl$_3$: | aluminium chloride |
| Eq.: | equivalents |
| CC: | column chromatography on silica gel |
| DCC: | N,N'-dicyclohexyl carbodiimide |
| THF: | tetrahydrofuran |
| TEA: | triethylamine |
| h: | hour(s) |
| HPLC: | high performance liquid chromatography |
| HBr: | hydrobromic acid |
| HCl: | hydrochloric acid |
| MgSO$_4$: | magnesium sulfate |
| NH$_4$HSO$_4$: | ammonium hydrogen sulfate |
| NaOH: | sodium hydroxide |
| NaCl: | sodium chloride |
| NaHCO$_3$: | sodium hydrogen carbonate |
| Na$_2$CO$_3$: | sodium carbonate |
| KOtBu: | potassium tert-butylate |
| LAH: | lithium aluminium hydride |
| HOBT (1-HBT): | 1-hydroxybenzotriazol |
| RT: | room temperature |
| TMSCN: | trimethylsilylcyanide |
| TBAB: | tetra-n-butylammoniumbromide |
| GC-MS: | gas chromatographic/mass spectrometric analysis |

"M" and "N" are concentrations in mol/l. "%" is wt.-% unless indicated otherwise. The yields of any compounds obtained in any steps of the process of the invention have not been optimized. Any temperatures were not corrected.

All compounds not explicitly described were either commercially available (e.g. from Acros, Avocado, Aldrich, Bachem, Fluka, Lancaster, Maybridge, Merck, Sigma, TCI, Oakwood etc.) (syntheses of these compounds may e.g. be researched in the "Symyx® Available Chemicals Database" of the company MDL, San Ramon, US) or the syntheses of these compounds has been already described by technical literature sources (experimental procedures may e.g. by researched in the "Reaxys®" database of the company Elsevier, Amsterdam, NL) or these compounds may be synthesized according to conventional procedures known to a person skilled in the art.

Silica gel 60 (0.010-0.063 mm; company: Merck, Darmstadt, Germany) was used as stationary phase for CC (column chromatography). Mixing ratios of any solvent or eluent mixtures are indicated in volume/volume. The analytical characterization of all compounds was performed by means of $^1$H-NMR spectroscopy and mass spectrometric analyses.

A process according to alternative A for the preparation of different stereoisomers of 3-(3-dimethylamino-1-ethyl-2-methyl-propyl)-phenol is depicted in the following Scheme A:

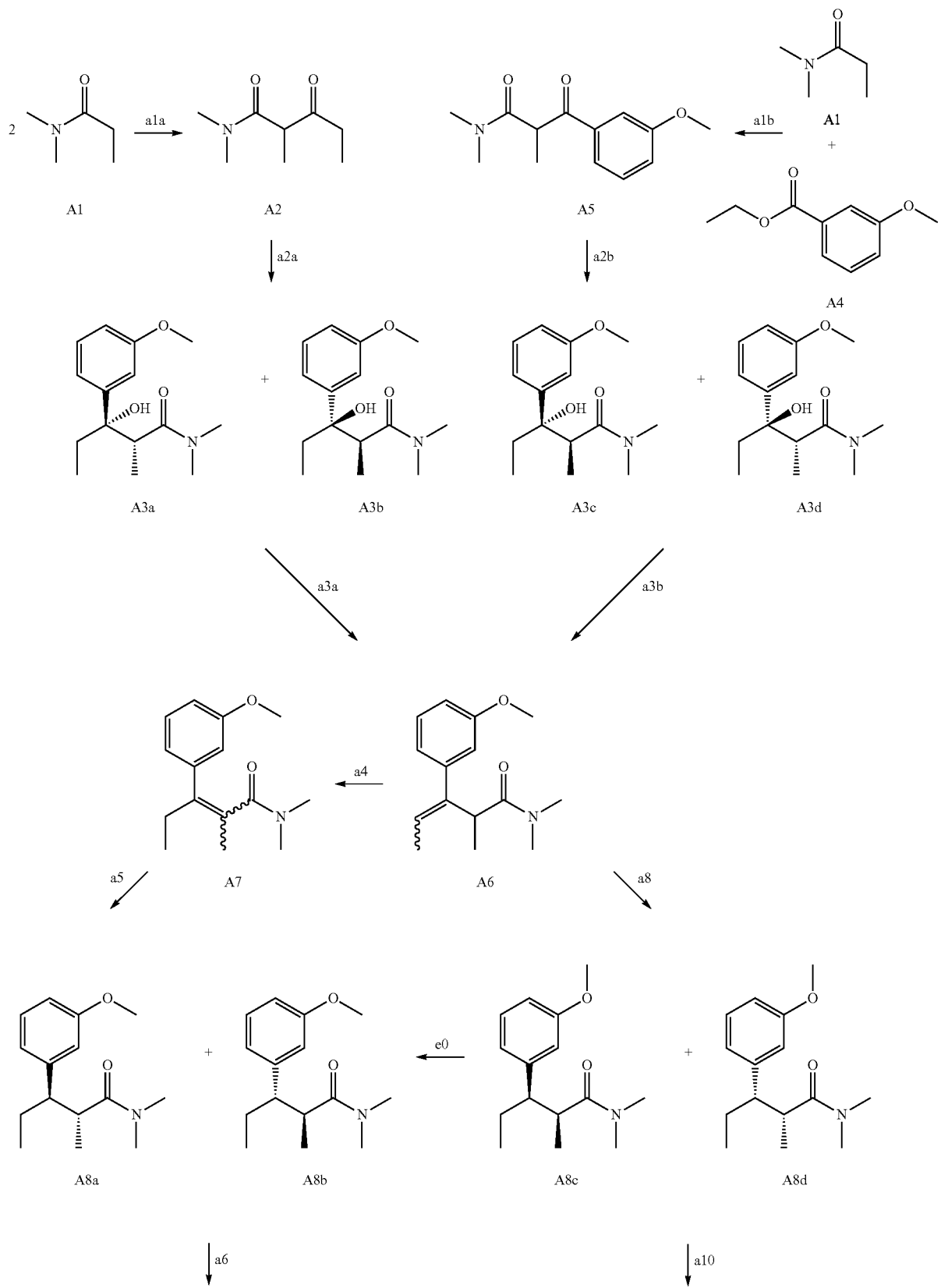
Scheme A

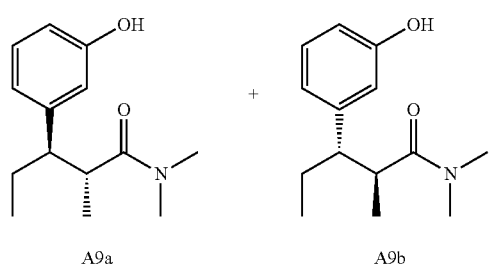
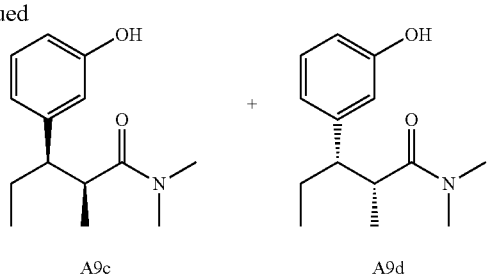

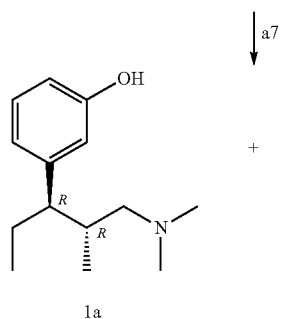
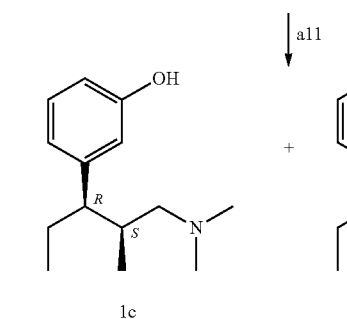

Step a1a: compound A2 (N,N-2-trimethyl-3-oxopentanamide)

32.1 ml (0.35 mol) phosphoryl trichloride (POCl$_3$) were dissolved in 100 mL of toluene. 32.6 ml (0.3 mol) N,N-dimethylpropionamide (A1) (dissolved in 50 mL toluene) were added to the resulting solution under stirring under an inert gas atmosphere. The reaction mixture was heated to 80° C. for 6 h, allowed to cool to RT and stirred for another 12 h at RT. After evaporation of toluene under reduced pressure, the resulting mixture was stirred for 2 h. 100 mL toluene were then added, the resulting mixture was cooled to below 0° C. and icy water (100 mL) was added. Then, 24 g of solid NaOH, dissolved in water, were added to the mixture. After 1 h of stirring, 47.7 g Na$_2$CO$_3$ as solid were added and the resulting mixture was stirred for 16 h at RT. The organic layer was separated, dried over MgSO$_4$ and distilled (0.8 bar, 78-82° C.). 10.8 g (46%) of A2 was obtained in form of a colorless solid.

Step a2a: compounds A3a and A3b ((2RS,3SR)-3-hydroxy-3-(3-methoxyphenyl)-N,N,2-trimethylpentanamide)

To 699 mg (29 mmol) of magnesium 20 mL of dry THF were added. A solution of 3.64 mL of 3-bromoanisole in 10 mL of dry THF was slowly added dropwise. After addition, the remaining suspension was refluxed for 2 h and then cooled to 0° C. 7.1 g (29 mmol) of anhydrous cerium (III) chloride were dissolved in 65 mL of dry THF and added to the reaction mixture which was then stirred for 90 minutes at 0° C. 3 g (19 mmol) of A2 (dissolved in 10 mL dry THF) were slowly added dropwise. After 1 h the reaction mixture was hydrolyzed by an aqueous saturated solution of NaHCO$_3$ at 10-15° C. The organic layer was separated and the aqueous layer was extracted with diethyl ether three times. The combined organic layers were dried over MgSO$_4$. The organic solvents were evaporated under reduced pressure and the remaining residue was dried in vacuo. CC (eluent: n-hexane/diethyl ether (1:4)) yielded 3.29 g (65%) of A3a and A3b in form of a yellowish oil.

Step a1b: compound A5 (3-(3-methoxyphenyl)-N,N,2-trimethyl-3-oxopropanamide)

To 2,2,6,6-tetramethylpiperidine (17.5 g, 125 mmol) in 50 ml dry THF were added dropwise 72 ml (115 mmol) of a n-buthyllithium solution in n-hexane (1.6 M) at −30° C. After 30 minutes of stirring, 5.0 g (50 mmol) N,N-dimethylpropionamide (A1) (dissolved in 50 mL dry THF) were added and the mixture was cooled to −70° C. and stirred for 1 h at this temperature. 22.5 g (125 mmol) ethyl-3-methoxybenzoate (dissolved in 30 mL dry THF) were slowly added dropwise and the resulting mixture was stirred for another 2 h at −70° C. After the mixture had been allowed to warm to RT, it was hydrolyzed by employing a diluted aqueous solution of HCl (36 mL). The mixture was then washed with diethyl ether several times. The combined organic layers were dried over MgSO$_4$. The organic solvents were evaporated under reduced pressure and the remaining residue was dried in vacuo. CC (eluent: n-hexane/ethyl acetate (1:4)) yielded 6.5 g (55%) of A5 in form of a colorless oil.

Step a2b: compounds A3c and A3d ((2RS,3RS)-3-hydroxy-3-(3-methoxyphenyl)-N,N,2-trimethylpentanamide)

2.4 g (6.4 mmol) anhydrous cerium (III) chloride were dissolved in 22 mL of dry THF. 2.13 mL (6.4 mmol) of a solution of ethyl magnesium bromide in diethyl ether (3 M) were added to the resulting solution at 0° C. and the mixture was stirred for 90 minutes at this temperature.

1 g (4.3 mmol) of A2 (dissolved in 5 mL dry THF) were slowly added dropwise. After 1 h of stirring the reaction mixture was hydrolyzed by employing an aqueous saturated solution of NaHCO$_3$ at 10-15° C. The organic layer was separated and the aqueous layer was extracted with diethyl ether three times. The combined organic layers were dried over MgSO$_4$. The organic solvents were evaporated under reduced pressure and the remaining residue was dried in vacuo. CC (eluent: n-hexane/diethyl ether (1:1)) yielded 740 mg (66%) of A3c and A3d in form of a yellowish oil.

Step a3a: compound A6 (Z,E-3-hydroxy-3-(3-methoxyphenyl)-N,N,2-trimethylpentanamide)

3.25 g (12 mmol) A3a and A3b were dissolved in 35 mL of an aqueous solution of HBr (47%) and stirred for 20 h. The reaction mixture was then cooled to 0° C. 50 mL of ethyl acetate and 50 mL of water were added and the resulting mixture was alkalized with solid $NaHCO_3$. The organic layer was separated and the aqueous layer was extracted with ethyl acetate several times. The combined organic layers were dried over $MgSO_4$. The organic solvent was evaporated under reduced pressure and the remaining residue was dried in vacuo. CC (eluent: n-hexane/diethyl ether (1:1)) yielded 1.61 g (54%) of A6 in form of a colorless oil.

Step a3b: compound A6 (Z,E-3-hydroxy-3-(3-methoxyphenyl)-N,N,2-trimethylpentanamide 3.25 g (12 mmol) A3c and A3d were dissolved in 35 mL of an aqueous solution of HBr (47%) and stirred for 20 h. The reaction mixture was then cooled to 0° C. 50 mL of ethyl acetate and 50 mL of water were added and the resulting mixture was alkalized with solid $NaHCO_3$. The organic layer was separated and the aqueous layer was extracted with ethyl acetate several times. The combined organic layers were dried over $MgSO_4$. The organic solvent was evaporated and the remaining residue was dried in vacuo. CC (eluent: n-hexane/diethyl ether (1:1)) yielded 2.68 g (90%) of A6 in form of a colorless oil.

Step a4: Compound A7 (Z, E-3-(3-methoxyphenyl)-N,N,2-trimethylpent-2-enamide)

700 mg (2.8 mmol) A6 were dissolved in 20 mL of dry THF. 318 mg (2.8 mmol) KOtBu were added to the resulting solution. The resulting mixture was refluxed for 3 h. After cooling to RT 50 mL of ethyl acetate and 50 mL of water were added. The layers of the resulting solution were separated and the aqueous layer was extracted twice with ethyl acetate. The combined organic layers were dried over $MgSO_4$. The organic solvent was evaporated under reduced pressure and the remaining residue was dried in vacuo. CC (eluent: n-hexane/diethyl ether (1:1)) yielded 430 mg (61%) of A7 in form of a colorless oil.

Step a5: Compounds A8a and A8b ((2RS,3RS)-3-(3-methoxyphenyl)-N,N,2-trimethylpentan-amide)

400 mg (1.6 mmol) A7 were placed in a hydrogenation apparatus and dissolved in 10 mL of methanol. 1 drop of concentrated HCl and a small amount of mg Pd/C (10% Pd) covering the tip of a spatula as catalyst were added under inert gas atmosphere. The resulting mixture was hydrogenated at room temperature under a $H_2$-pressure of 1 bar for 6 h (91 mL $H_2$ were used). The solids were filtered off and washed with methanol. The methanol portion and the filtrate were combined. After evaporation of the organic solvents, the residue was suspended in a mixture of water and diethyl ether (30 mL each). A diluted aqueous solution of NaOH was added to the mixture until alkalization. The layers of the resulting solution were separated and the aqueous layer was washed three times with diethyl ether. The combined organic layers were dried over $MgSO_4$. The organic solvent was evaporated under reduced pressure and the remaining residue was dried in vacuo. CC (eluent: n-hexane/diethyl ether (1:1)) yielded 160 mg (45%) of A8a and A8b in form of a colorless oil. As a side product, A8c and A8d could be obtained in a yield of 25% (80 mg) in form of a colorless oil.

Step e0: Compounds A8a and A8b ((2RS,3RS)-3-(3-methoxyphenyl)-N,N,2-trimethylpentan-amide)

200 mg (0.8 mmol) of a mixture of A8c and A8d were dissolved in 4 mL of dry THF. 90 mg (0.8 mmol) KOtBu were added to the resulting solution. The resulting mixture was refluxed for 3 h. After cooling to RT 50 mL of ethyl acetate and 50 mL of water were added. The layers of the resulting solution were separated and the aqueous layer was extracted twice with ethyl acetate. The combined organic layers were dried over $MgSO_4$. The organic solvent was evaporated under reduced pressure and the remaining residue was dried in vacuo yielding a mixture of A8a/A8b and the starting material A8c/A8d (GC-MS: 1:4) in form of a yellowish oil.

Step a6: Compounds A9a and A9b ((2RS,3RS)-3-(3-hydroxyphenyl)-N,N,2-trimethylpentan-amide)

To 202 mg D,L-methionine (1.4 mmol) and 2 mL methane sulfonic acid were added 170 mg (0.68 mmol) of A8a and A8b. The reaction mixture was stirred for 6 h. Water and ethyl acetate (20 mL each) were added. After neutralization with solid $NaHCO_3$ the layers were separated from each other. The aqueous layer was extracted twice with ethyl acetate. The combined organic layers were dried over $MgSO_4$. The organic solvents were evaporated under reduced pressure and the remaining residue was dried in vacuo. 160 mg (99%) of A9a and A9b were obtained in form of a colorless oil.

Step a7: Compounds 1a and 1b ((2R,S,3RS)-3-(1-(dimethylamino)-2-methylpentan-3-yl)-phenol)

To 1.6 mL (0.35 mmol) of LAH-THF solution (2.3 M) were added 120 mg (0.90 mmol) of $AlCl_3$. The resulting mixture was stirred for 45 minutes at RT. 170 mg (0.72 mmol) of A9a and A9b (dissolved in 5 ml of dry THF) were added to the mixture at RT. The resulting mixture was then refluxed for 1 h. Then the reaction mixture was hydrolyzed by addition of 20 mL of an aqueous solution of $NaHCO_3$ (10%). 20 mL of diethyl ether were added and the layers were separated from each other and the aqueous layer was extracted twice with diethyl ether. The combined organic layers were dried over $MgSO_4$. The organic solvent was evaporated under reduced pressure and the remaining residue was dried in vacuo. 1a and 1b were obtained in form of a colorless oil. The hydrochloride salts of 1a and 1b were obtained by addition of trimethylsilylchloride (76 µl) to a solution of 1a and 1b in acetone (yield: 100 mg (54%) in form of a colorless solid).

Step a8: Compound A8c and A8d ((2RS,3SR)-3-(3-methoxyphenyl)-N,N,2-trimethylpentan-amide)

1 g (4 mmol) A6 were placed in a hydrogenation apparatus and dissolved in 10 mL of methanol. 1 drop of concentrated HCl and 250 mg Pd/C (10% Pd) as catalyst were added under inert gas atmosphere. The resulting mixture was hydrogenated at room temperature under a $H_2$-pressure of 1 bar for 6 h (118 mL $H_2$ were used). The solids were filtered out and washed with methanol. The methanol portion and the filtrate were combined. After evaporation of the organic solvents, the residue was suspended in a mixture of water and diethyl ether (30 mL each). Diluted aqueous solution of NaOH was added to the mixture until alkalization. The layers of the resulting solution were separated and the aqueous layer was washed three times with diethyl ether. The combined organic layers were dried over $MgSO_4$. The organic solvent was evaporated and the remaining residue was dried in vacuo. CC (eluent: n-hexane/diethyl ether (1:1)) yielded 1 g (99%) of A8c and A8D as a yellowish oil.

Step a10: Compound A9c and A9d ((2RS,3SR)-3-(3-hydroxyphenyl)-N,N,2-trimethylpentan-amide)

To 170 mg D,L-methionine (1.4 mmol) and 2 mL methane sulfonic acid were added 200 mg (0.80 mmol) of A8c and A8d. The reaction mixture was stirred for 6 h. Water and ethyl acetate (20 mL each) were added. After neutralization with solid $NaHCO_3$ the layers were separated from each other. The aqueous layer was extracted twice with ethyl acetate. The combined organic layers were dried over $MgSO_4$. The organic solvents were evaporated under reduced pressure and the remaining residue was dried in vacuo. 170 mg (90%) of A9c and A9d were obtained in form of a colorless oil.

Step a11: Compound 1c and 1d ((2RS,3SR)-3-(1-(dimethylamino)-2-methylpentan-3-yl)phenol)

To 1.56 mL (0.32 mmol) of LAH-THF solution (2.3 M) were added 113 mg (0.85 mmol) of AlCl$_3$. The resulting mixture was stirred for 45 minutes at RT. 160 mg (0.68 mmol) of A9c and A9d (dissolved in 5 ml of dry THF) were added to the mixture at RT. The resulting mixture was then refluxed for 1 h. Then the reaction mixture was hydrolyzed by addition of 20 mL of an aqueous solution of NaHCO$_3$ (10%). 20 mL of diethyl ether were added and the layers were separated from each other and the aqueous layer was extracted twice with diethyl ether. The combined organic layers were dried over MgSO$_4$. The organic solvent was evaporated under reduced pressure and the remaining residue was dried in vacuo. 1c and 1d were obtained in form of a colorless oil. The hydrochloride salts of 1c and 1d were obtained by addition of trimethylsilylchloride (76 µl) to a solution of 1c and 1d in diethyl ether (yield: 100 mg (54%) in form of a colorless solid).

A process according to alternative B for the preparation of 3-(3-methoxyphenyl)-2-methyl-pentyl-dimethylamine is depicted in the following Scheme B:

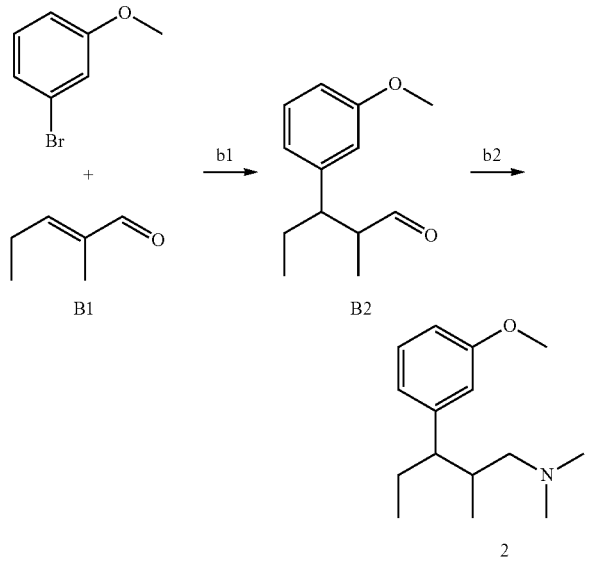

Scheme B

Step b1: Compound B2 (3-(3-methoxyphenyl)-2-methylpentanal)

Alternative a)

To 1.46 g (0.06 mol) of magnesium were added 50 mL of dry THF. 5 drops of 3-bromoanisole were added to this mixture and the resulting suspension was refluxed until the reaction started. Then, a solution of 7.63 mL of 3-bromoanisole (0.06 mol) in 15 mL of dry THF was slowly added dropwise, thereby maintaining a constant reflux of the reaction mixture. After addition and refluxing of the reaction mixture for another hour, the mixture was cooled to −70° C. At this temperature 11.4 g (0.06 mol) copper(I) iodide (CuI) and 30 mL of dry THF were added. The mixture was then allowed to warm to around −65 to −60° C. At this temperature, commercially available 2-methyl-2-pentenal, dissolved in 15 mL of dry THF were added slowly to the reaction mixture. After stirring for 1 h at −65–−60° C., the reaction mixture was allowed to warm to 0° C. The reaction mixture was hydrolyzed by addition of 50 mL of a saturated aqueous solution of NH$_4$HSO$_4$. The mixture was then extracted three times with 100 mL of diethyl ether. The combined organic layers were dried over MgSO$_4$. The organic solvent was evaporated and the remaining residue was dried in vacuo. CC (eluent: diisopropyl ether/n-hexane (1:30)) yielded 2.3 g (29%) of B2 as a colorless oil.

Alternative b)

10.2 ml 3-bromoanisole (82 mmol) were dissolved in 30 mL of a mixture of dry diethyl ether/toluene (1:1) and cooled to −70° C. A solution of n-butyl lithium in n-hexane (55 mL, 1.6 M) was then added to the mixture and the reaction mixture was stirred for 4 h at this temperature. 3.6 g (80 mmol) of copper(I) cyanide (CuCN) were then added and the mixture was stirred another 30 minutes at −70° C. 4.6 mL (40 mmol) of pre-cooled 2-methyl-2-pentenal and 5.9 mL of a BF$_3$-diethyl ether-solution (47 mmol) in 30 mL of a mixture of dry diethyl ether/toluene (1:1) were slowly added dropwise at this temperature. The reaction mixture was the allowed to warm to RT and stirred or 16 h. 25 mL of a saturated aqueous solution of NH$_4$OH were then added and the mixture was extracted with diethyl ether three times. The combined organic layers were dried over MgSO$_4$. The organic solvent was evaporated and the remaining residue was dried in vacuo. 8 g (99%) of a colorless oil were obtained which—according to GC-MS analysis—contained 24% of B2.

Step b2: Compound 2 (3-(3-ethoxyphenyl)-2-methyl-pentyl-dimethylamine)

To 4.8 mL of a methanolic solution of dimethylamine (9.6 mmol, 2M) were added 5 ml of methanol, 0.40 g (4.8 mmol) of dimethylamine hydrochloride and 0.18 g Na(CN)BH$_3$ (4.8 mmol). Then, 1 g (4.8 mmol) B2, dissolved in 15 ml methanol, were added dropwise and the resulting mixture was stirred for 20 h at RT. The reaction mixture was poured into 15 mL of a cooled aqueous solution of HCl (16%) and extracted with dichloromethane. The layers were separated from each other and the aqueous layer was alkalized with solid KOH, saturated with NaCl and then extracted with dichloromethane. The dichloromethane layer was separated and dried over MgSO$_4$. The organic solvents were evaporated under reduced pressure and the remaining residue was dried in vacuo. 0.21 g (19%) of 2 in form of a colorless oil were obtained.

In Scheme C a process according to alternative C for the preparation of 3-(2-(aminomethyl)cyclohexyl)phenol is depicted and described below.

Scheme C:

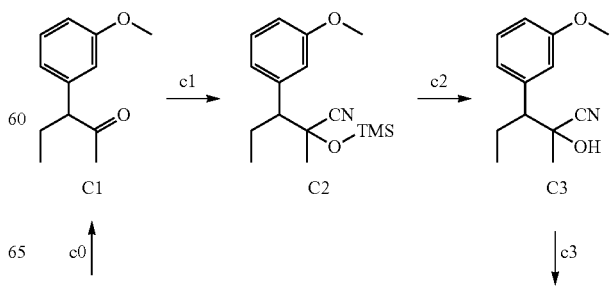

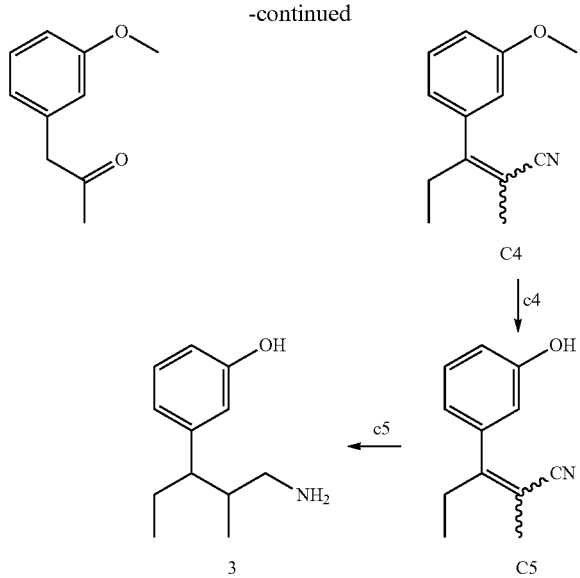

Step c0: compound C1 (3-(3-methoxyphenyl)pentan-2-one)

To 2 mL (13 mmol) of commercially available 1-(3-methoxyphenyl)propan-2-one (e.g. from Lancaster)) were added 6.5 mL of an aqueous solution of NaOH (50%), a small amount of TBAB covering the tip of a spatula and 1.1 mL (14.1 mmol) of ethyl iodide. The resulting mixture was stirred for 12 h. After addition of 30 mL distilled water and 30 mL of toluene, the mixture was stirred for another hour. The layers were separated and the organic layer was washed with a saturated aqueous solution of NaCl. The layers were separated and the organic layer was dried over MgSO₄. The organic solvent was evaporated under reduced pressure and the remaining residue was dried in vacuo. 2.2 g (86%) of C1 were obtained in form of a yellow oil.

Step c1: Compound C2 (3-(3-methoxyphenyl)-2-methyl-2-(trimethylsilyloxy)pentanenitrile)

To a small amount covering the tip of a spatula of ZnI₂ were added 4.4 g (23 mmol) of C1 and 3.4 mL (25 mmol) TMSCN. The resulting mixture was stirred for 60 minutes. After addition of 40 mL of dry n-hexane, the mixture was refluxed for 15 minutes. After addition of a small amount of charcoal covering the tip of a spatula, the resulting mixture was refluxed for another 15 minutes. The reaction mixture was then filtered. The solvents of the filtrate were then evaporated under reduced pressure. 6.5 g (97%) of C1 were obtained in form of a grey oil.

Step c2: Compound C3 (2-hydroxy-3-(3-methoxyphenyl)-2-methylpentanenitrile)

To 120 mg (0.41 mmol) C2 were added 1.5 mL of dry methanol and the resulting mixture was cooled to 0° C. 300 μl of an aqueous solution of HCl (5 M) were added at this temperature and the mixture was stirred for 3 h at RT. The organic solvents were evaporated under reduced pressure and a mixture of water and diethyl ether was added to the remaining residue. NaHCO₃ was added until the aqueous layer had been alkalized. The layers were separated and the aqueous layer was extracted several times with diethyl ether. The combined organic layers were dried over MgSO₄. The organic solvent was evaporated under reduced pressure and the remaining residue was dried in vacuo. 89 mg (99%) of C3 were obtained in form of a colorless oil.

Step c3: Compounds C4 (Z,E-3-(3-methoxyphenyl)-2-methylpent-2-enenitrile)

To 3.72 g (17 mmol) C3 were added 80 mL of toluene, 40 mL of pyridine and 81 mL of phosphoryl chloride (POCl₃), dissolved in 16 mL pyridine. The resulting mixture was refluxed for 1 h. After cooling, the reaction mixture was poured into ice water. Ethyl acetate was then added and the layers were separated from each other. The aqueous layer was extracted twice with ethyl acetate. The combined organic layers were washed with distilled water, with a diluted aqueous solution of NaOH and were then dried over MgSO₄. The organic solvents were evaporated under reduced pressure and the remaining residue was dried in vacuo. CC (eluent: n-hexane/diethyl ether (10:1)) yielded 1.71 g (50%) of Z-regioisomer of C4 well as 850 mg (25%) of the E-regioisomer of C4, each as a yellowish oil.

Step c4: Compound C5 (Z,E-3-(3-hydroxyphenyl)-2-methylpent-2-enenitrile)

To 0.13 g D,L-methionine and 1.6 mL methane sulfonic acid were added 120 mg (0.6 mmol) of C4. The reaction mixture was stirred for 16 h. Water and ethyl acetate were added. After neutralization with solid NaHCO₃ the layers were separated from each other. The aqueous layer was extracted twice with ethyl acetate. The combined organic layers were dried over MgSO₄. The organic solvents were evaporated under reduced pressure and the remaining residue was dried in vacuo. CC (eluent: ethyl acetate/n-hexane (1:5)) yielded 90 g (80%) of C5 (mixture of Z,E-regioisomers) in form of a yellow oil.

Step c5: Compound 3 (3-(1-amino-2-methylpentan-3-yl)phenol)

70 mg (3.5 mmol) C5 were dissolved in 5 mL of dry methanol and placed in a hydrogenation apparatus. A small amount of a commercially available Raney-Nickel (Ra—Ni) suspension (in water) covering the tip of a spatula was added to the mixture. The resulting mixture was hydrogenated at room temperature under a H₂-pressure of 2 bar for 12 h (use of H₂: 128 ml). The solids were filtered off and the solvents of filtrate were evaporated under reduced pressure and the remaining residue was dried in vacuo. 70 mg (98%) of compound 3 were obtained in form of a brownish oil.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:
1. A process for preparing a compound according to formula (I)

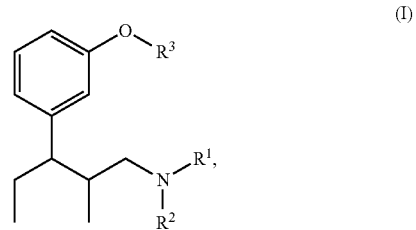

wherein
R¹, R² and R³ are each independently selected from the group consisting of H and $C_{1-4}$-aliphatic residues,
or a physiologically acceptable acid addition salt thereof, according to alternative A said process comprising the steps of:
(a-I) hydrogenating a compound according to formula (A-I-a):

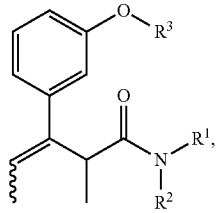

wherein R¹, R² and R³ in each case have the above defined meanings,
to a compound according to formula (A-II):

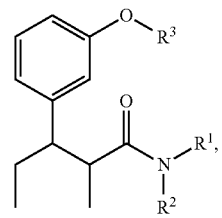

wherein R¹, R² and R³ have the above defined meanings,
(a-II) reducing the compound according to formula (A-II) to a compound according to formula (I), and
(a-III) optionally converting the compound according to formula (I) into a physiologically acceptable acid addition salt thereof.

2. A process according to claim 1, wherein said compound is in the form of an isolated stereoisomer.

3. A process according to claim 2, wherein said compound is in the form of an isolated enantiomer or diastereomer.

4. A process according to claim 1, wherein said compound is in the form of a mixture of stereoisomers in any mixing ratio.

5. A process according to claim 4, wherein said compound is in the form of a racemic mixture of stereoisomers.

6. A process according to claim 1, wherein in alternative A:
the hydrogenation step (a-I) is effected via heterogeneous or homogeneous catalysis in the presence of hydrogen, and
the reduction step (a-II) is carried out by employing at least one metal hydride, at least one borane or hydrogen in combination with a catalyst as reducing agent.

7. A process according to claim 1, wherein in alternative A:
the hydrogenation step (a-I) is effected via heterogeneous catalysis in the presence of hydrogen by employing at least one catalyst selected from the group consisting of Raney nickel, palladium, palladium on carbon, platinum, platinum on carbon, ruthenium on carbon and rhodium on carbon, and
the reduction step (a-II) is carried out by employing as reducing agent at least one metal hydride selected from the group consisting of lithium aluminium hydride, sodium borohydride, diisobutyl aluminium hydride, and selectrides.

8. A process according to claim 1, wherein alternative A further comprises a step (a-IV) in which a compound according to formula (A-0):

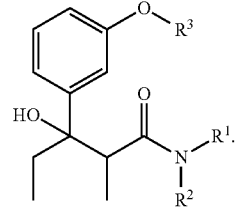

wherein R¹, R² and R³ are each independently selected from the group consisting of H and $C_{1-4}$-aliphatic residues,
is subjected to a dehydration reaction to obtain the compound according to formula (A-I-a).

9. A process according to claim 1, wherein:
R¹ and R² in formula (I) are each independently selected from the group consisting of H, methyl, ethyl, n-propyl, isopropyl, n-butyl, sec.-butyl, isobutyl and, tert.-butyl; and
R³ in formula (I) is selected from the group consisting of H, methyl, ethyl, n-propyl, isopropyl, n-butyl, sec.-butyl, isobutyl and tert.-butyl.

10. A process according to claim 9, wherein:
R¹ and R² in formula (I) are each independently selected from the group consisting of H and methyl; and
R³ in formula (I) is selected from the group consisting of H and methyl.

11. A process according to claim 1, for preparing a compound according to formula (Ib)

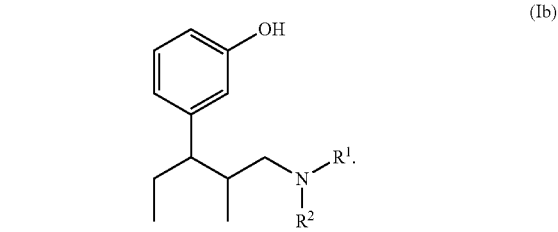

wherein R¹ and R² are each independently selected from the group consisting of H and $C_{1-4}$-aliphatic residues
or a physiologically acceptable acid addition salt thereof.

12. A process according to claim 11, wherein said process comprises:
deprotecting a compound according any one of the formulas (A-0), (A-I-a), (A-II), (B-I), (C-0-I), (C-0-II), (C-I), (I) and (Ia) in which R³ is other than H, to yield the compound according to formula (Ib), and
optionally converting the thus obtained compound according to formula (Ib) into a physiologically acceptable acid addition salt thereof.

13. A process according to claim 11, wherein said compound is in the form of an isolated stereoisomer.

14. A process according to claim 11, wherein said compound is in the form of a mixture of stereoisomers in any mixing ratio.

* * * * *